United States Patent
Herold et al.

(10) Patent No.: US 9,333,219 B2
(45) Date of Patent: May 10, 2016

(54) METHOD TO TREAT OR PREVENT HERPESVIRUS INFECTIONS

(71) Applicant: ALBERT EINSTEIN COLLEGE OF MEDICINE OF YESHIVA UNIVERSITY, Bronx, NY (US)

(72) Inventors: Betsy Herold, Rowayton, CT (US); Natalia Cheshenko, Bronx, NY (US)

(73) Assignee: Albert Einstein College of Medicine, Inc., Bronx, NY (US)

(*) Notice: Subject to any disclaimer, the term of this patent is extended or adjusted under 35 U.S.C. 154(b) by 0 days.

(21) Appl. No.: 14/415,333

(22) PCT Filed: Jul. 25, 2013

(86) PCT No.: PCT/US2013/051987
§ 371 (c)(1),
(2) Date: Jan. 16, 2015

(87) PCT Pub. No.: WO2014/022185
PCT Pub. Date: Feb. 6, 2014

(65) Prior Publication Data
US 2015/0190419 A1    Jul. 9, 2015

Related U.S. Application Data

(60) Provisional application No. 61/679,169, filed on Aug. 3, 2012.

(51) Int. Cl.
| | |
|---|---|
| *A61K 48/00* | (2006.01) |
| *C07H 21/02* | (2006.01) |
| *C07H 21/04* | (2006.01) |
| *A61K 31/713* | (2006.01) |
| *C07K 14/035* | (2006.01) |
| *C12N 15/113* | (2010.01) |
| *A61K 31/685* | (2006.01) |
| *A61K 31/7105* | (2006.01) |

(52) U.S. Cl.
CPC ............ *A61K 31/713* (2013.01); *A61K 31/685* (2013.01); *A61K 31/7105* (2013.01); *C07K 14/035* (2013.01); *C12N 15/1133* (2013.01); *C12N 15/1137* (2013.01); *C12N 2310/14* (2013.01)

(58) Field of Classification Search
CPC ..... A61K 48/00; C12N 15/111; C12N 15/113
See application file for complete search history.

(56) References Cited

U.S. PATENT DOCUMENTS

| | | | |
|---|---|---|---|
| 2001/0049113 A1 | 12/2001 | Lee et al. | |
| 2004/0186118 A1 | 9/2004 | Bryant et al. | |
| 2005/0260199 A1* | 11/2005 | Compton et al. | 424/144.1 |
| 2009/0239932 A1 | 9/2009 | Sale et al. | |
| 2011/0182910 A1 | 7/2011 | Medof et al. | |
| 2012/0100109 A1 | 4/2012 | Zhang et al. | |
| 2012/0190676 A1 | 7/2012 | Moorman et al. | |

FOREIGN PATENT DOCUMENTS

| | | |
|---|---|---|
| WO | 2010134939 A2 | 11/2010 |
| WO | 2012103524 A2 | 8/2012 |

OTHER PUBLICATIONS

Bertrand et al. (Biochemical and Biophysical Research Communications, 296, 2002, 1000-1004).*
PCT International Search Report and Written Opinion, dated Feb. 3, 2014 in connection with PCT International Application No. PCT/US2013/51987, 13 pages.
Sun M et al., entitled "Akt Plays a Critical Role in Replication of Nonsegmented Negative-Stranded RNA Viruses," J Virol. 2008, 82(1):105-14.
Dunn E F et al., entitled "AKT Inhibitor Akt-IV Blocks Virus Replication through an AKT-Independent Mechanism," J Virol. 2009, 83(22):11665-72.
Cheshenko N et al., entitled "HSV activates Akt to trigger calcium release and promote viral entry: novel candidate target for treatment and suppression," FASEB J. Jul. 2013, 27, 2584-2599.
Liu T C et al., entitled "Herpes Simplex Virus Us3(-) Mutant as Oncolytic Strategy and Synergizes with Phosphatidylinositol 3-Kinase-Akt-Targeting Molecular Therapeutics," Clin Cancer Res. 2007, 13(19):5897-902.

* cited by examiner

*Primary Examiner* — Amy Bowman
(74) *Attorney, Agent, or Firm* — Amster, Rothstein & Ebenstein LLP

(57) ABSTRACT

Methods and compositions are provided for inhibiting or treating a herpesvirus infection in a subject using inhibitors of mammalian Akt.

14 Claims, 10 Drawing Sheets

METHOD TO TREAT OR PREVENT HERPESVIRUS INFECTIONS

CROSS-REFERENCE TO RELATED APPLICATIONS

This application is a U.S. national stage entry under 35 U.S.C. §371 of PCT International Patent Application No. PCT/US2013/051987, filed Jul. 25, 2013, which claims benefit of U.S. Provisional Application No. 61/679,169, filed Aug. 3, 2012, the contents of each of which are incorporated herein by reference into the subject application.

STATEMENT OF GOVERNMENT SUPPORT

This invention was made with government support under grant number AI-061679 awarded by the National Institutes of Health. The government has certain rights in the invention.

BACKGROUND OF THE INVENTION

Throughout this application various publications are referred to in parentheses. Full citations for the publications may be found at the end of the specification. The disclosures of each of these publications, and also the disclosures of all patents, patent application publications and books recited herein, are hereby incorporated by reference in their entirety into the subject application to more fully describe the art to which the subject invention pertains.

Herpesviruses, especially herpes simplex viruses (HSV), are a major global health problem, the leading cause of genital ulcerative disease, neonatal and sporadic infectious encephalitis, and a major co-factor for HIV infection (Tronstein, 2011). Acyclovir treatment reduces the morbidity and mortality associated with encephalitis and suppressive therapy with acyclovir or its prodrug, valacyclovir, reduces mucocutaneous recurrences and the risk of transmission (Corey, 2004). However, acyclovir resistance is a problem in some populations and there is no effective vaccine (Belshe, 2012). Thus, novel approaches to prevent and treat HSV are needed (Wilson, 2009). Development of new strategies requires an understanding of the cellular and molecular events required for infection.

The present invention address the need to treat and to prevent herpesvirus infections, including herpes simplex virus.

SUMMARY OF THE INVENTION

A method is provided of treating a viral infection in a subject, comprising administering to the subject an amount of an inhibitor of Akt, or an amount of an inhibitor of a viral glycoprotein B, C, D or H, effective to treat a viral infection.

A method is also provided of treating a herpesvirus infection in a subject, comprising administering to the subject an amount of an inhibitor of Akt effective to treat a herpesvirus infection.

A method is also provided of preventing a herpesvirus infection of a subject, comprising prophylactically administering to the subject an amount of an inhibitor of Akt effective to prevent a herpesvirus infection, or an amount of an inhibitor of a herpesvirus glycoprotein B, C, D or H effective to prevent a herpesvirus infection.

Also provided is a method of preventing a herpesvirus infection of a subject, comprising prophylactically administering to the subject an amount of an inhibitor of Akt effective to prevent a herpesvirus infection.

Also provided is a composition comprising an amount of an inhibitor of Akt effective to treat or prevent a herpesvirus infection.

Also provided is an inhibitor of Akt for treating or preventing a herpesvirus infection in a subject.

Also provided is an inhibitor of a viral glycoprotein B, C, D or H, for treating or preventing a herpesvirus infection in a subject.

Additional objects of the invention will be apparent from the description which follows.

DETAILED DESCRIPTION OF THE INVENTION

Figures 1A, 1B, 1C, 1D:
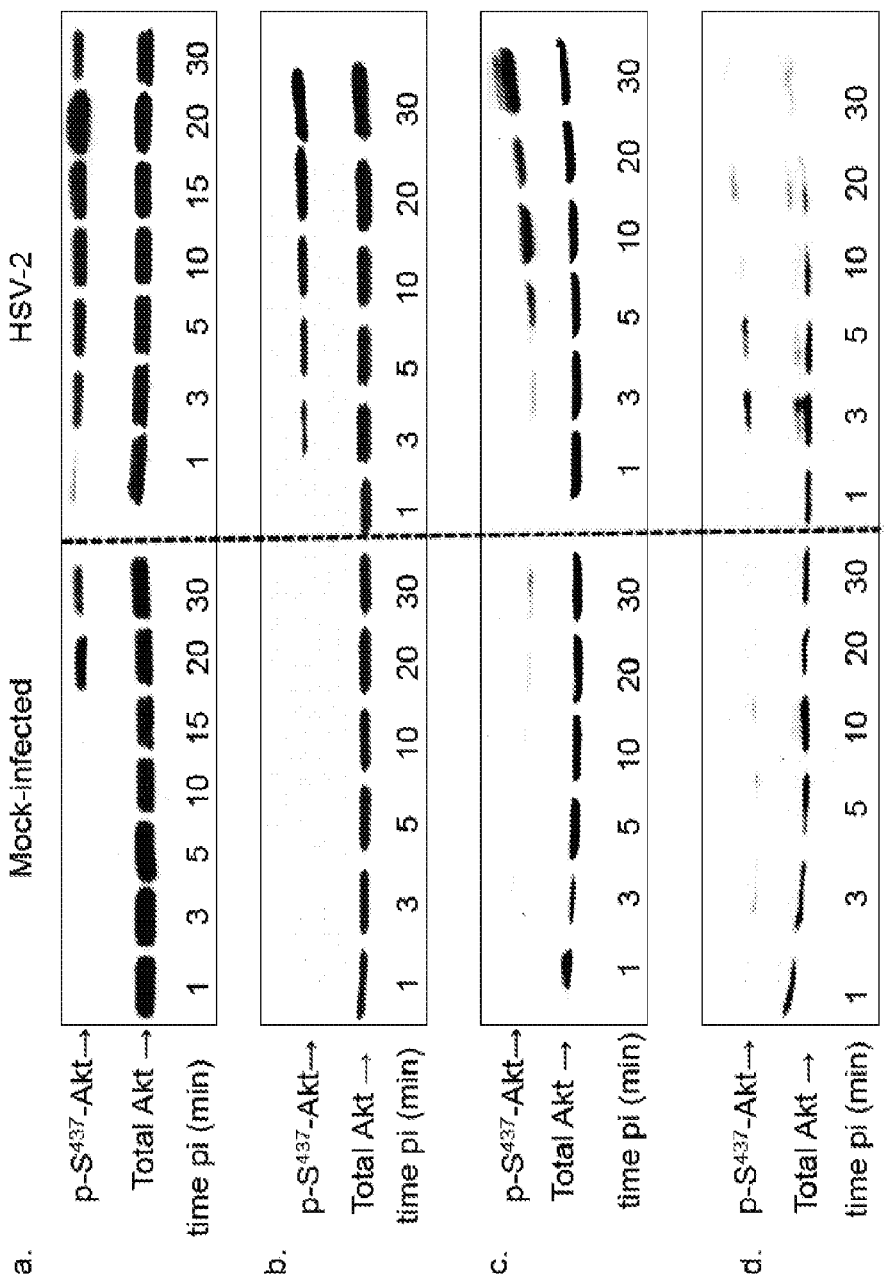
FIG. 1A-1D. HSV induces Akt phosphorylation. CaSki (a), SK-N-SH (b), HaCAT (c) or End1/E6E7 (d) cells were exposed to serum free media (mock-infection) or infected with HSV-2(G) diluted in serum-free media (moi 10 pfu/cell) and cell lysates were prepared for Western blotting at the indicated times pi. Blots were incubated with anti-pS473-Akt1/2/3 and anti-total Akt1/2/3. Representative blots from at least 3 independent experiments are shown.

A method is provided of treating a viral infection in a subject, comprising administering to the subject an amount of an inhibitor of Akt, or an amount of an inhibitor of a viral glycoprotein B, C, D or H, effective to treat a viral infection. In an embodiment, the virus is a herpesvirus.

In an embodiment, the method comprises administering to the subject an amount of an inhibitor of Akt effective to treat a herpesvirus infection.

In an embodiment, the method comprises administering to the subject an amount of an inhibitor of a viral glycoprotein C, B, D or H effective to treat a herpesvirus infection. In a preferred embodiment, an inhibitor of viral glycoprotein B or D is administered. In a preferred embodiment, the inhibitor is of viral glycoprotein B or D and disrupts or reduces the interaction of a glycoprotein B with an Akt. In an embodiment, the inhibitor of the viral glycoprotein is an RNAi nucleic acid. In an embodiment, the RNAi nucleic acid is an shRNA or siRNA directed against a herpesvirus glycoprotein B, C, D or H.

A method is provided of preventing a herpesvirus infection of a subject, comprising prophylactically administering to the subject an amount of an inhibitor of Akt effective to prevent a herpesvirus infection, or an amount of an inhibitor of a herpesvirus glycoprotein B, C, D or H effective to prevent a herpesvirus infection.

Also provided is a method is provided of treating a herpesvirus infection in a subject, comprising administering to the subject an amount of an inhibitor of Akt effective to treat a herpesvirus infection.

A method is also provided of preventing a herpesvirus infection of a subject, comprising prophylactically administering to the subject an amount of an inhibitor of a herpesvirus glycoprotein B, C, D or H effective to prevent a herpesvirus infection.

A method is also provided of preventing a herpesvirus infection of a subject, comprising prophylactically administering to the subject an amount of an inhibitor of Akt effective to prevent a herpesvirus infection.

The methods disclosed herein involving subjects can be used with any species capable of being infected by a member of the herpesviridae family. In a preferred embodiment of the methods, the subject is a mammalian subject. Most preferably, the mammal is a human.

In an embodiment of the methods, the subject has not been diagnosed as having a herpes infection. In an embodiment, the subject does not have, or has not been diagnosed as having, an HIV infection. In an embodiment, the subject does not have, or has not been diagnosed as having, a cancer. In an embodiment, the subject does not have, or has not been diagnosed as having, a tumor. In an embodiment, the subject does not have, or has not been diagnosed as having, diabetes. In an embodiment, the subject does not have, or has not been diagnosed as suffering from a leishmaniasis. In an embodiment, the subject does not have, or has not been diagnosed as suffering from a protozoal infection. In an embodiment, the subject does not have, or has not been diagnosed as suffering from a fungal infection.

Inhibitors of Akt are known in the art, for example, miltefosine, perifosine, MK-2206 dihydrochloride, inhibitor VIII, PHT-427, AT7867, CCT128930, A-674563, Triciribine phosphate (NSC-280594), PF-04691502, VQD-002, honokiol. All of these are encompassed by the present invention unless otherwise stated. In an embodiment, any one or more of these recited inhibitors is excluded. In an embodiment, miltefosine is 2-(hexadecoxy-oxido-phosphoryl)oxyethyl-trimethylazanium.

As used herein, "Akt", also known as Protein Kinase B (PKB), is a serine/threonine-specific protein kinase known in the art. In an embodiment, Akt is the serine-threonine protein kinase Akt1 encoded by the AKT 1 gene. In a preferred embodiment, the Akt inhibitor inhibits Akt1. In a preferred embodiment, the Akt inhibitor inhibits Akt2. In a preferred embodiment, the Akt inhibitor inhibits Akt3. In an embodiment, the Akt inhibitor inhibits two of Akt1, Akt2 and Akt3. In an embodiment, the Akt inhibitor inhibits all of Akt1, Akt2 and Akt3. In a most preferred embodiment, the Akt is mammalian, and the inhibitor of Akt is an inhibitor of mammalian Akt. On an embodiment, the Akt is a human Akt. In an embodiment, the inhibitor of Akt is an inhibitor of human Akt.

In an embodiment of the methods, the herpesvirus is a herpes simplex virus, a cytomegalovirus, an Epstein Barr virus, a human herpesvirus-6, a human herpesvirus-7, a Varicella zoster virus, or a Kaposi's sarcoma-associated herpesvirus. In a preferred embodiment of the methods, the herpesvirus is herpes simplex virus-1 or is herpes simplex virus-2.

In an embodiment of the methods, the subject has neonatal encephalitis, sporadic encephalitis, and/or genital ulcerative disease. In an embodiment of the methods, the subject is at risk of neonatal encephalitis or of sporadic encephalitis. In an embodiment of the methods, the subject has a herpesvirus infection that is resistant to acyclovir and/or valacyclovir.

In an embodiment of the methods, the subject has neurological symptoms from a herpesvirus infection.

In an embodiment of the methods, the inhibitor of Akt is in a pharmaceutical composition. A pharmaceutical composition preferably comprises one or more substances which act as a pharmaceutically acceptable carrier.

In an embodiment of the methods, the subject does not have a herpesvirus infection, and the methods prevents infection of the subject with the herpesvirus. In an embodiment of the methods, the subject has a herpesvirus infection, and the method prevents further herpesvirus infection in the subject. In an embodiment of the methods, the subject has a latent herpesvirus infection.

In an embodiment of the methods, the inhibitor of Akt, or the inhibitor of a viral glycoprotein B, C, D or H, is applied systemically to the subject. In an embodiment of the methods, the inhibitor of Akt, or the inhibitor of a viral glycoprotein B, C, D or H, is applied to topically the subject. In an embodiment of the methods, the inhibitor of Akt, or the inhibitor of a viral glycoprotein B, C, D or H, is applied to a mucous membrane of the subject. In an embodiment of the methods, the inhibitor of Akt, or the inhibitor of a viral glycoprotein B, C, D or H, is applied to a genitalial surface of the subject.

In an embodiment of the methods, the inhibitor of Akt is a small organic molecule of 2,000 daltons or less. In an embodiment of the methods, the inhibitor of Akt is a small organic molecule of 1,500 daltons or less. In an embodiment of the methods, the inhibitor of Akt is a small organic molecule of 1,000 daltons or less. In an embodiment of the methods, the inhibitor of Akt is a small organic molecule of 500 daltons or less. In a preferred embodiment of the methods, the inhibitor of Akt is miltefosine.

In an embodiment, the inhibitor is an RNAi nucleic acid, such as an siRNA or shRNA. In an embodiment of the methods, the inhibitor of Akt is a nucleic acid capable of hybridizing with a nucleic acid encoding Akt, or is an oligonucleotide aptamer capable of hybridizing with a nucleic acid encoding Akt. Such a nucleic acid capable of hybridizing with a nucleic acid encoding Akt includes siRNAs and shRNAs. In an embodiment, the siRNA (small interfering RNA) as used in the methods or compositions described herein comprises a portion which is complementary to an mRNA sequence encoding an Akt. For example, an mRNA sequence encoded by NCBI Reference Sequence: NM_005163.1, and the siRNA would be effective to inhibit expression of Akt1. For example, an mRNA sequence encoded by NCBI Reference Sequence: NM_001626.3, and the siRNA would be effective to inhibit expression of Akt2. For example, an mRNA sequence encoded by NCBI Reference Sequence: NM_181690.2, and the siRNA would be effective to inhibit expression of Akt3. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. In an embodiment, the overhang is UU. The siRNA can be 5' phosphorylated or not and may be modified with any of the known modifications in the art to improve efficacy and/or resistance to nuclease degradation. In a non-limiting embodiment, the siRNA can be administered such that it is transfected into one or more cells.

In one embodiment of the methods, a siRNA of the invention comprises a double-stranded RNA comprising a first and second strand, wherein one strand of the RNA is at least 80%, at least 85%, at least 90%, at least 95% or is 100% complementary to a portion of an RNA transcript of a gene an Akt. Thus, in an embodiment, the invention encompasses an siRNA comprising a 19, 20 or 21 nucleotide first RNA strand which is 80, 85, 90, 95 or 100% complementary to a 19, 20 or 21 nucleotide portion, respectively, of an RNA transcript of an Akt gene, e.g. Akt1. In embodiment, the second RNA strand of the double-stranded RNA is also 19, 20 or 21 nucleotides, respectively, a 100% complementary to the first strand. In another embodiment, a siRNA of the invention comprises a double-stranded RNA wherein one strand of the RNA comprises a portion having a sequence the same as a portion of 18-25 consecutive nucleotides of an RNA transcript of a gene encoding an Akt. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length.

Where a numerical range is provided herein, it is understood that all numerical subsets of that range, and all the individual integers contained therein, are provided as part of the invention. Thus, a siRNA which is from 28 to 56 nucleotides in length includes the subset of primers which are 28 to 34 nucleotides in length, the subset of primers which are 29 to 50 nucleotides in length, etc., as well as a siRNA which is 28 nucleotides in length, a siRNA which is 29 nucleotides in length, a siRNA which is 30 nucleotides in length, etc. up to and including a siRNA which is 56 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In one embodiment, RNAi inhibition of Akt is effected by a short hairpin RNA ("shRNA"). The shRNA can be introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, in the present case Akt. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

In an embodiment of the methods, the inhibitor of a viral glycoprotein B, C, D or H is an inhibitor of a herpesvirus glycoprotein B, C, D or H, respectively. In a preferred embodiment of the methods, the inhibitor is an inhibitor of a herpesvirus glycoprotein B.

Also provided is a composition comprising an amount of an inhibitor of Akt effective to treat or prevent a herpesvirus infection. In a preferred embodiment, the inhibitor of Akt is miltefosine. In a preferred embodiment, the composition is a pharmaceutical composition. In an embodiment, the composition further comprises a pharmaceutically acceptable carrier.

Also provided is an inhibitor of Akt for treating or preventing a herpesvirus infection in a subject.

In an embodiment of the compositions, or of the inhibitor, the inhibitor of Akt is a small organic molecule of 2,000 daltons or less. In an embodiment, the inhibitor of Akt is a small organic molecule of 1,500 daltons or less. In an embodiment, the inhibitor of Akt is a small organic molecule of 1,000 daltons or less. In an embodiment, the inhibitor of Akt is a small organic molecule of 500 daltons or less. In an embodiment, the small organic molecule is not an oligomer or polymer. In a preferred embodiment, the inhibitor of Akt is miltefosine.

In an embodiment of the compositions, or of the inhibitor, the inhibitor of Akt is a nucleic acid capable of hybridizing with a nucleic acid encoding Akt or an oligonucleotide aptamer capable of hybridizing with a nucleic acid encoding Akt.

In a preferred embodiment of the compositions, or of the inhibitor, the inhibitor of Akt is an inhibitor of mammalian Akt.

Also provided is an inhibitor of a viral glycoprotein B, C, D or H, for treating or preventing a herpesvirus infection in a subject. In an embodiment, the virus is a herpesvirus and the viral glycoprotein is a herpesvirus glycoprotein B, C, D or H.

Also provided is a method of identifying an inhibitor of herpesvirus infection comprising contacting an Akt with an agent and experimentally determining the activity of the Akt in the presence of the agent and in the absence of the agent, and identifying the agent as in inhibitor or not of herpesvirus infection, wherein a determination of greater activity of AKT in the absence of the agent than in the presence of the agent indicates that the agent is an inhibitor of herpesvirus infection, and wherein a determination of no change in, or a decrease in, activity of AKT in the absence of the agent as compared to in the presence of the agent indicates that the agent is an not an inhibitor of herpesvirus infection. In an embodiment, the agent is a small organic molecule of 2,000 daltons or less. In an embodiment, the method is for identifying an inhibitor of herpesvirus infection of a subject species, from which species the Akt of the method is obtained or has an amino acid sequence identical to the Akt thereof. In an embodiment, the species is a mammalian species.

"Acyclovir" (9-[2-hydroxymethyl]guanine), as used herein, is a nucleoside analog which selectively inhibits the replication of herpes simplex virus (types 1 and 2) and varicella zoster virus. valacyclovir is a prodrug for acyclovir.

As used herein, "treating" a herpesvirus infection means ameliorating one or more symptoms of a herpesvirus infection and/or lessening the level of herpesvirus infection in a subject. Symptoms of herpes simplex virus (HSV) infection include sores, for example on a mucosal membrane such as the lips (e.g. cold sores). Other symptoms of HSV infection include genital herpes, herpetic whitlow, herpes gladiatorum, ocular herpes (keratitis), herpes esophagitis, cerebral herpes infection encephalitis, and Mollaret's meningitis.

As used herein an "aptamer" is a single-stranded oligonucleotide or oligonucleotide analog that binds to the particular target molecule, either Akt or a nucleic acid encoding an Akt, and inhibits the function or expression thereof, respectively.

As used herein an "inhibitor of a viral glycoprotein" is an agent, such as an RNA, nucleic acid or a small organic molecule, that disrupts the physiological function of a viral glycoprotein. In an embodiment, the inhibitor is of glycoprotein B and it disrupts and/or reduces the interaction between Akt and a viral glycoprotein B.

As used herein, "preventing" a herpesvirus infection of a subject means reducing the extent of, or stopping, herpesvirus infection of an uninfected subject, or reducing the extent of, or stopping, further herpesvirus infection of a herpesvirus infected subject.

As used herein, a "herpesvirus" is one of a family of viruses also known as herpesviridae in the art, which includes the family members herpes simplex virus (1 and 2), cytomegalovirus, Epstein-Barr virus, human herpesvirus-6, human herpesvirus-7, varicella zoster virus, and Kaposi's sarcoma-associated herpesvirus.

"And/or" as used herein, for example, with option A and/or option B, encompasses the embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Results

HSV entry is complex and for both serotypes requires the concerted activities of the envelope glycoproteins D (gD), B (gB) and hetero-oligomers of H and L (gH-gL) (Spear, 2004; Heldwein, 2008). However, the precise role each plays and the cellular pathways that mediate entry are not fully understood. In prior studies, it was demonstrated that in human epithelial and neuronal cells, both serotypes (HSV-1 and HSV-2) trigger a rapid increase in the intracellular calcium ($Ca^{2+}$) concentration ($[Ca^{2+}]$) and that blockade of this response prevents viral entry (Cheshenko, 2003). Specifically, the increase in $[Ca^{2+}]$ and viral entry were blocked following: (i) chelation of intracellular (but not extracellular) $Ca^{2+}$; (ii) treatment with the inositol triphosphate receptor (IP3R) antagonist, 2-aminoethoxydiphenyl borate, or (iii) silencing of the IP3R with small interfering RNA (siRNA) (Cheshenko, 2003; Cheshenko, 2007). Subsequent confocal studies identified two spatially distinct $Ca^{2+}$ responses: one at the plasma membrane and the other a global cytosolic response (Cheshenko, 2007).

Using small interfering RNA (siRNA) strategies to silence cellular proteins in CaSki (cervical epithelial cell line) and viral variants deleted in the essential envelope glycoproteins (Cheshenko, 2003; Cheshenko, 2007), it was found that binding of viral particles to syndecan-2, a major family of heparan sulfate proteoglycans, and engagement of the gD co-receptor, nectin-1, triggered the release of a small amount of $Ca^{2+}$ near the plasma membrane, which seems to initiate the entry process. However, completion of the entry process and intracellular delivery of viral capsids required the release of global intracellular $Ca^{2+}$ stores, activation of IP3Rs, and the full complement of essential viral envelope glycoproteins (gB, gD, and gH-gL). The IP3Rs are located predominantly in the endoplasmic reticulum (ER) and are the major components of the cytosolic $Ca^{2+}$ regulatory machinery. Confocal studies demonstrated that silencing of IP3Rs resulted in virus being trapped within the plasma membrane (Cheshenko, 2007). Together, these findings suggest a central role for $Ca^{2+}$ in promoting HSV entry. However, the initial signals at the cell surface that trigger the plasma membrane $Ca^{2+}$ response and how it is linked to the release of IP3R-regulated ER $Ca^{2+}$ stores have not been delineated.

Two signaling pathways are involved in the intracellular generation of inositol phosphates (Berridge, 2009). The first is initiated by one of several phosphoinositide-specific phospholipase C proteins (PLC), which trigger the hydrolysis of phosphatidylinositol-4,5-bisphosphate to release the second messengers diacylglycerol and inositol triphosphate (IP3). IP3 binds to its receptors, located primarily on the ER, to activate $Ca^{2+}$ release, which is characterized by temporal oscillations and propagating waves (Venkatachalam, 2002). The second signaling pathway is initiated by phosphoinositide 3-kinase (PI3K), an enzyme that phosphorylates inositol lipids generating phosphatidylinositol 3,4-bisphosphate (PIP2) and phosphatidylinositol 3,4,5-trisphosphate (PIP3) (Patterson, 2005). These molecules play critical roles in regulating the serine/threonine protein kinase, Akt (also called protein kinase B). Akt possesses a pleckstrin homology (PH) domain, which when bound by PIP3, becomes anchored at the plasma membrane where it may be activated in response to phosphorylation by cellular kinases or following autophosphorylation at the Ser-473 site (Alessi, 1997; Harlan, 1994; McManus, 2004; Toker, 2000). Activated Akt, in turn, phosphorylates a number of key substrates involved in the promotion of cell survival, proliferation, and growth. Recent studies demonstrated that the IP3Rs are one of the substrates activated by Akt and that Akt potentiates IP3R-mediated $Ca^{2+}$ release (Hwang, 2009; Hwang, 2009).

Results

HSV triggers rapid phosphorylation of Akt: To assess whether exposure to HSV activates Akt signaling, CaSki cells, a human cervical epithelial cell line, were infected with HSV-2 diluted in serum-free media or serum-free media alone (mock-infection) and cell lysates were prepared at different times post-infection (pi). Phosphorylation of Akt was assessed by Western blot; blots were first probed with a monoclonal antibody specific for phosphorylated Akt and then stripped and probed with a rabbit polyclonal antibody to total Akt. An increase in p-S473-Akt relative to mock-infected cells was consistently observed as early as one minute following exposure to HSV-2 and peaked ~10-20 minutes post-viral exposure (FIG. 1a). A more modest increase in pAkt was also observed in mock-infected CaSki cells at the later time points, which may reflect the physiology of this cell line. Indeed, CaSki cells harbor multiple copies of integrated HPV DNA and may have altered Akt expression. Therefore, the observations were extended to include SK-N-SH cells, a human neuroblastoma cell line, HaCAT cells, a spontaneously immortalized human kerinatocyte cell line, and End2/E6E7 cells, human endocervical cells immortalized with a vector containing HPV-16 E6/E7 (Fichorova, 1999). HSV-2 induced Akt phosphorylation in all of the cell types, although the relative amounts of Akt expressed and the kinetics of the response varied (FIGS. 1b-d). Similar results were also obtained in response to HSV-1 (not shown).

Figures 2A, 2B, 2C, 2D, 2E:
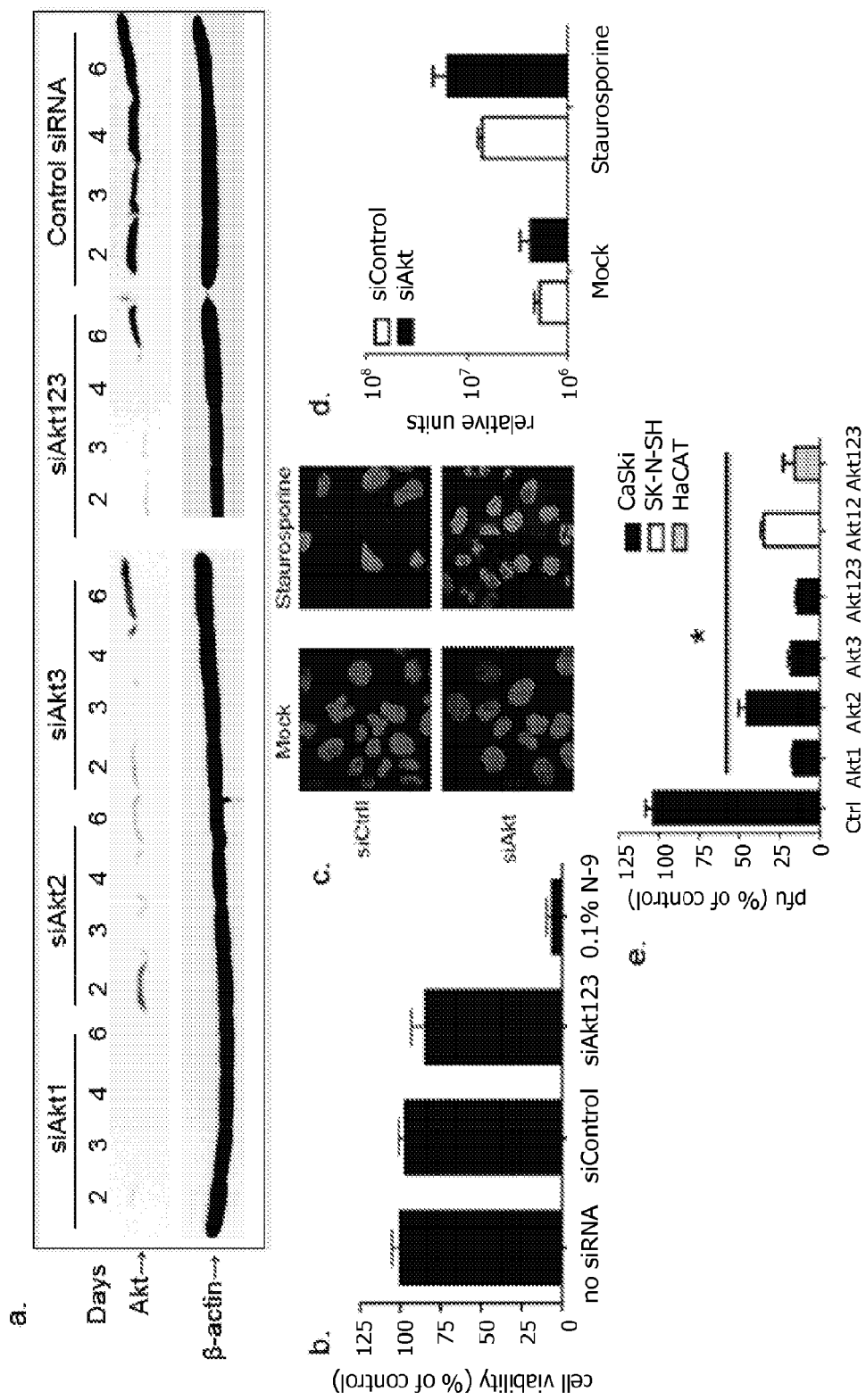
FIG. 2A-2E: siRNAs targeting Akt silence protein expression, are not cytotoxic, and block HSV-2 plaque formation. Cells were transfected with individual siRNA targeting Akt1, Akt2, Akt3 or a mixture of the three different sequences of Akt or a control siRNA at concentration of 10 nM (3.30 nM of each siRNA for the cocktail) and protein expression evaluated by preparing Western blots and probing for Akt and β-actin (a). Cellular proliferation was evaluated 72 h after transfection using the CellTiter96 kit. Nonoxynol-9 (N-9) (0.01%) was included as a toxicity control. Optical density was measured and the percentage of viability was determined based on the no siRNA control level (b). CaSki cells were transfected with siAkt123 or siControl for 72 h and either mock treated or incubated with 1 μM staurosporine for 4 h. Cells were stained for apoptosis and the percentage of late apoptotic cells determined by counting 5 random fields per treatment. Apoptotic cells are magenta and nuclei are blue. Representative images (c) and means±SEM are shown (d). Cells were transfected with the indicated siRNAs and 72 h post-transfection, were infected with serial dilutions of HSV-2(G). Viral plaques were counted 2 days pi. (e) Results are presented as pfu on siRNA-transfected cells (various siRNAs listed on x-axis) as a percentage of pfu on cells transfected with control siRNA. Data are means±SEM of a minimum of three independent experiments conducted in duplicate. Only wells in which the number of plaques ranged between 25-200 plaques were used to calculate the viral titer. The asterisks indicate $p<0.001$ relative to control.

Silencing of Akt reduces HSV infection: To explore the role Akt phosphorylation plays in infection and, specifically, viral entry, CaSki cells were transfected with siRNA targeting each isoform of Akt, a cocktail of siRNA targeting the three isoforms of Akt (Akt1/2/3) (Testa, 2001), or a nonspecific control siRNA. The impact of siRNA on Akt protein expression was evaluated by performing Western blots at 2, 3, 4 and 6 days post-transfection. A reduction in Akt protein expression was observed as early as 2 days post-transfection, which persisted for at least 6 days; siAkt1 was the most effective (FIG. 2a). Silencing was not cytotoxic (nonoxynol-9 (N-9) was used as a positive toxicity control) (FIG. 2b) and had little effect on the number of cells undergoing spontaneous apoptosis, but led to a modest increase in apoptosis in response to stauroporine as assessed by DNA fragmentation (FIG. 2c,d). Silencing also did not induce the expression of IFN-α (not shown). However, silencing significantly inhibited viral plaque formation by as much as 90% relative to cells transfected with nonspecific control siRNA (p<0.001, ANOVA) (FIG. 2e). Transfection with siAkt2 alone had more modest inhibitory effects, which is consistent with the more modest reduction in Akt protein expression observed in these cells. Transfection of SK-N-SH and HaCAT cells with siRNA targeting Akt123 (confirmed by Western blots, not shown) also significantly inhibited HSV infection (FIG. 2e).

Figures 3A, 3B, 3C:
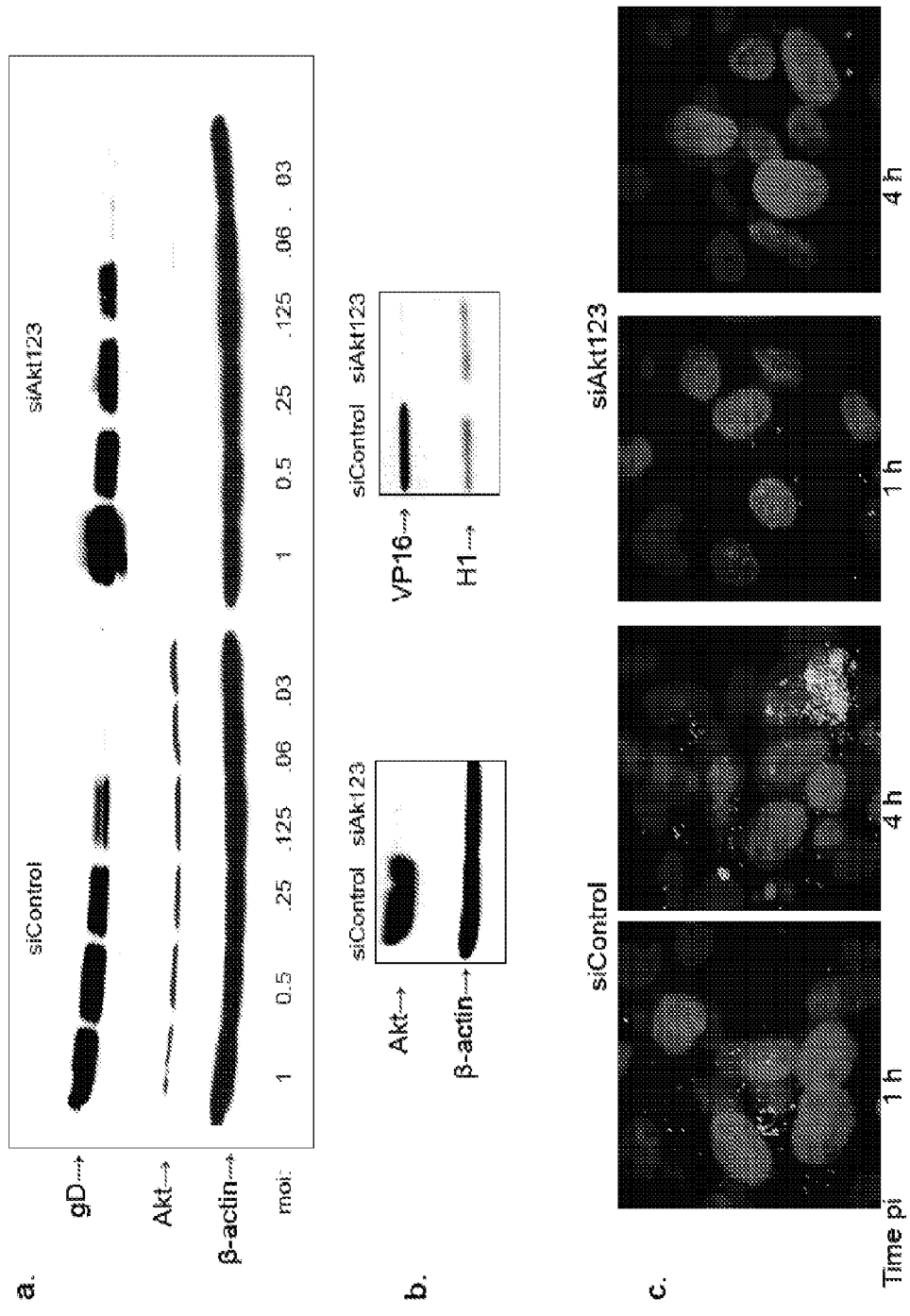
FIG. 3A-3C: Silencing of Akt inhibits viral entry independent of viral binding. Transfected CaSki cells were exposed to serial dilutions of HSV-2(G) at the moi (pfu/cell) indicated for 5 h at 4° C. The cell-bound viral particles were detected by analyzing Western blots of cell lysates for gD; blots were also probed with antibodies to total Akt (to assess silencing) and β-actin (control for protein loading) (a). Cells were transfected with siControl or siAkt123 and silencing confirmed by preparing Western blots of cell lysates 48 h post-transfection and probing for total Akt and β-actin expression (b). The siRNA-transfected cells were inoculated with HSV-2(G) and nuclear extracts were prepared and analyzed for the presence of the viral tegument protein VP16 by Western blotting; blots were probed with antibodies to histone-H1 as a nuclear extract control. Blots shown are representative of results obtained in 3 independent experiments (c). Transfected CaSki cells were exposed to purified dual-labeled HSV-1 K26GFP (viral capsids are lighter gray and viral envelopes are labeled red with DiI) and at the indicated times pi, cells were fixed and viewed by confocal microscopy; nuclei were stained with DAPI (darker gray). Representative images are shown (c).

Silencing of Akt prevents HSV entry post-binding: To identify whether Akt inhibition impairs viral binding or entry, specific assays were performed, focusing on CaSki cells. Cells were transfected with control siRNA or siRNAs targeting Akt123 and then exposed to serial dilutions of HSV-2 at 4° C., a temperature permissive for binding but not entry, and binding monitored by preparing Western blots and probing for the viral envelope glycoprotein D as previously described (Cheshenko, 2002). Silencing of Akt123 had no discernible impact on HSV-2 binding (FIG. 3a).

Two independent approaches were applied to determine if Akt contributes to viral entry. VP16 is a viral tegument protein, which is delivered to the nucleus following HSV entry, and thus its nuclear transport provides a surrogate of entry. Cells were transfected with siRNA (Akt123 or control) and 72 h later, were infected with HSV-2. After incubation for 45 minutes, nuclear extracts were prepared and evaluated for VP16 by Western blot; histone H1 was included as a control for the nuclear extracts (FIG. 3b). Silencing of Akt reduced the nuclear transport of VP16, which is consistent with a block to viral entry. To more directly assess the impact of Akt silencing on viral entry, confocal studies were conducted with purified K26GFP, an HSV-1 viral variant in which GFP has been fused in frame with the gene for the viral capsid protein VP26 (Desai, 1998). For these studies, the viral envelope was labeled with the fluorescent long-chain carbocyanine dye, DiI (Lakadamyali, 2003). This enables discrimination between viral envelopes (red) and capsids (green). Cells were transfected with siRNA (control or Akt123) and 72 h later, the cells were infected with the envelope-labeled GFP virus (moi ~5 pfu/cell). Cells were harvested 1 and 4 h pi and and 50-100 cells were viewed by confocal microscopy; nuclei were stained with DAPI (blue). Viral capsids were readily detected in the majority of siControl cells (73% and 82% 1 and 4 h pi, respectively), whereas viral capsids were detected in few siAkt cells (7% and 5.5%) (FIG. 3c). In other studies, the cells were harvested 15, 30 or 60 min pi, fixed and stained with EZ-Link sulfosuccinimidobiotin (EZ-Link) to detect cellular plasma membranes rather than staining nuclei. Viral envelopes (red) were easily detected co-localized with the plasma membrane (blue) (merge: purple) in both siControl and siAkt cells. However, capsids released from the viral envelope were only observed in the siControl cells.

Figures 4A, 4B, 4C, 4D, 4E:
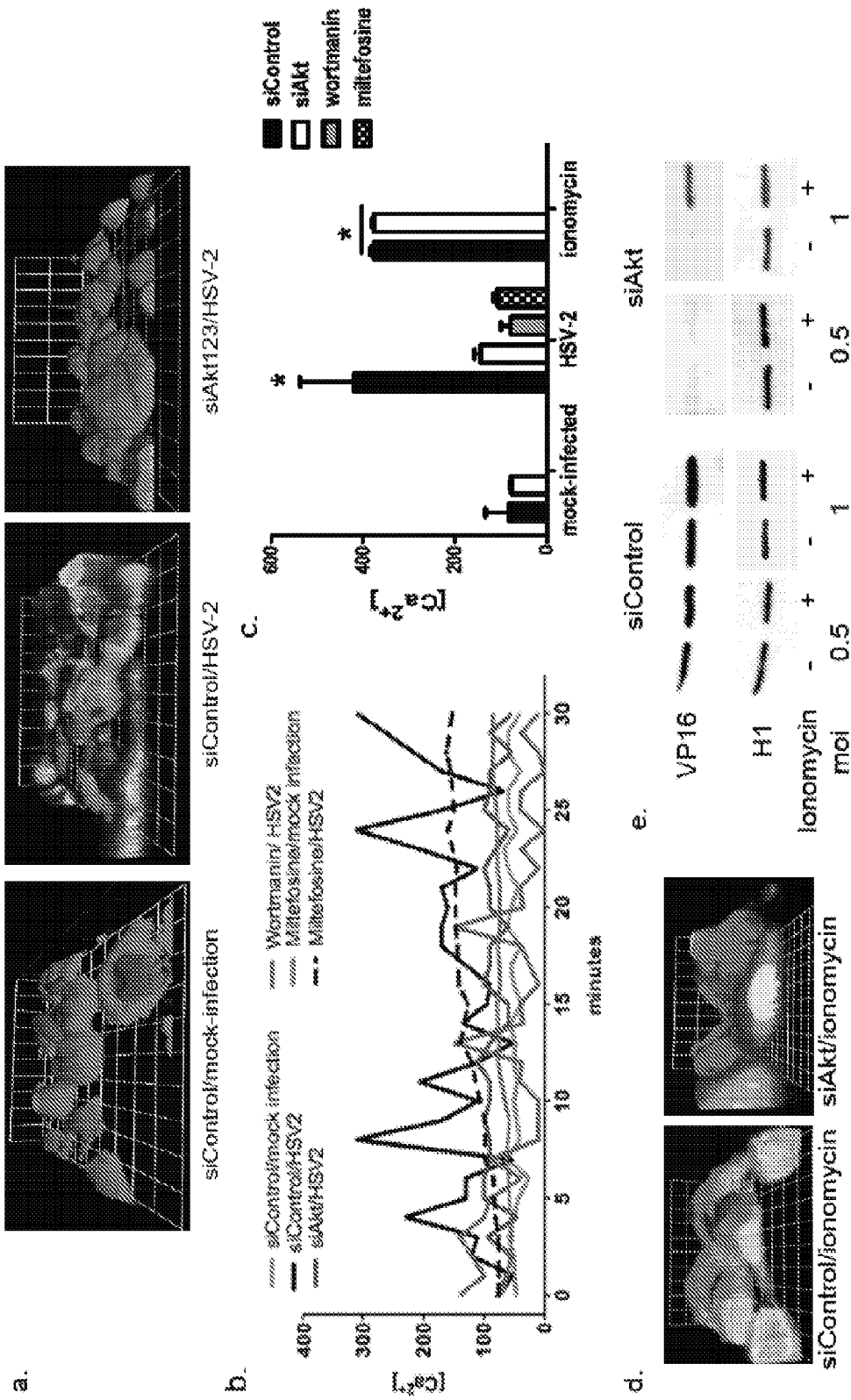
FIG. 4A-4E: Akt is required for HSV-induced calcium release and treatment with the ionophore, ionomycin, partially overcomes the block to infection in Akt-silenced cells. CaSki cells were loaded with Calcium Green 72 h post-transfection with the indicated siRNA and synchronously mock-infected or infected with purified HSV-2(G). Live images were acquired 3 min post-temperature shift to 37° C. For these xyz images, the plasma membranes are red (medium gray in grayscale), nuclei are blue (darkest gray in grayscale), and $Ca^{2+}$ is green (lighter gray in grayscale); colocalization of $Ca^{2+}$ and plasma membrane is yellow (lightest gray in grayscale). Representative images from 4 independent experiments are shown; the grid bars indicate a distance of 9.2 micrometers (a). Transfected cells were loaded with fura-2, infected with purified HSV-2 (moi 2 pfu/cell) or mock-infected and the kinetics of $Ca^{2+}$ response monitored. The mean intracellular $[Ca^{2+}]$ for $5\times10^4$ cells over the first 30 minutes was quantified; control cells were also pretreated with wortmannin or miltefosine and then infected with HSV-2 (b). The cumulative $[Ca^{2+}]$ released over 1 hour was calculated from 4 wells, each containing $5\times10^4$ cells (mock-infected, HSV-2 infected in the absence or presence of wortmannin or miltefosine, or following treatment of uninfected cells with 1 μM of ionomycin) (c). The asterisk indicates p<0.001 compared to mock-infected cells. CaSki cells were loaded with Calcium Green 72 h post-transfection with the indicated siRNA and then treated with 1 μM of ionomycin and live images were acquired (d). Silenced cells were treated with ionomycin or buffer (0.4% DMSO) immediately prior to infection with 0.5 or 1 pfu/cell of HSV-2 and nuclear extracts were prepared 45 min pi and analyzed for the presence of VP16 as a surrogate for viral entry. Blots were also scanned for histone H1 as a control (e).

Akt is required for HSV-induced $Ca^{2+}$ responses: To determine if Akt plays a role in the HSV-induced $Ca^{2+}$ responses associated with HSV entry, cells were transfected with siControl or siAkt123 and then 48 h post-transfection, the cellular membranes (red) and nuclei (blue) were labeled, cells were loaded with Calcium Green, and then synchronously infected with virus. HSV-2 (moi 5 pfu/cell) was allowed to bind for 4 h at 4° C., unbound virus removed by washing, and the cells were then placed in a temperature-regulated chamber for imaging; ~50-100 cells from random fields were imaged. Within 3 minutes following a shift in the temperature to 37° C., membrane (yellow) and global (green) intracellular $Ca^{2+}$ responses were detected in the majority of HSV-infected cells that had been transfected with a control siRNA. In contrast $Ca^{2+}$ release was observed in few (5-10%) of the HSV-infected cells that had been transfected with siAkt (FIG. 4a)

While confocal microscopy allows one to detect responses in individual cells and identify the subcellular localization of $Ca^{2+}$ responses, it is not quantitative. Therefore, quantitative kinetic fluorometric studies were conducted in parallel. Transfected CaSki cells (siControl or siAkt123) were loaded with fura-2, infected with purified HSV-2(G) (moi 2 pfu/cell) and the kinetics of $Ca^{2+}$ response monitored over the first hour following infection; the mean intracellular $[Ca^{2+}]$ for $5\times10^4$ cells at each time point was quantified (FIG. 4b, c). HSV-2 triggered a rapid and significant increase in intracellular $[Ca^{2+}]$ within the first few minutes following infection of control cells; additional waves were observed over the first hour (p<0.001, ANOVA). In contrast, cells transfected with siAkt showed little or no $Ca^{2+}$ response to HSV-2. Pretreatment of cells with wortmannin or miltefosine, inhibitors of the PI3K/Akt signaling pathway (Ruiter, 2003) also blocked the HSV-induced $Ca^{2+}$ response.

In parallel studies, the transfected cells were treated with 1 µM of ionomycin, a $Ca^{2+}$ ionophore. Ionomycin triggered the release of a comparable amount of Ca2+ from the siRNA-transfected cell populations as evidenced by confocal imaging and fluorometry (FIG. 4c, d), indicating intact intracellular stores. Moreover, ionomycin treatment partially restored the susceptibility to HSV entry in Akt-silenced cells as evidenced by the detection of nuclear VP16 in ionomycin treated (but not buffer treated) cells following exposure to 1 pfu/cell (FIG. 4e).

Figures 5A, 5B, 5C, 5D:
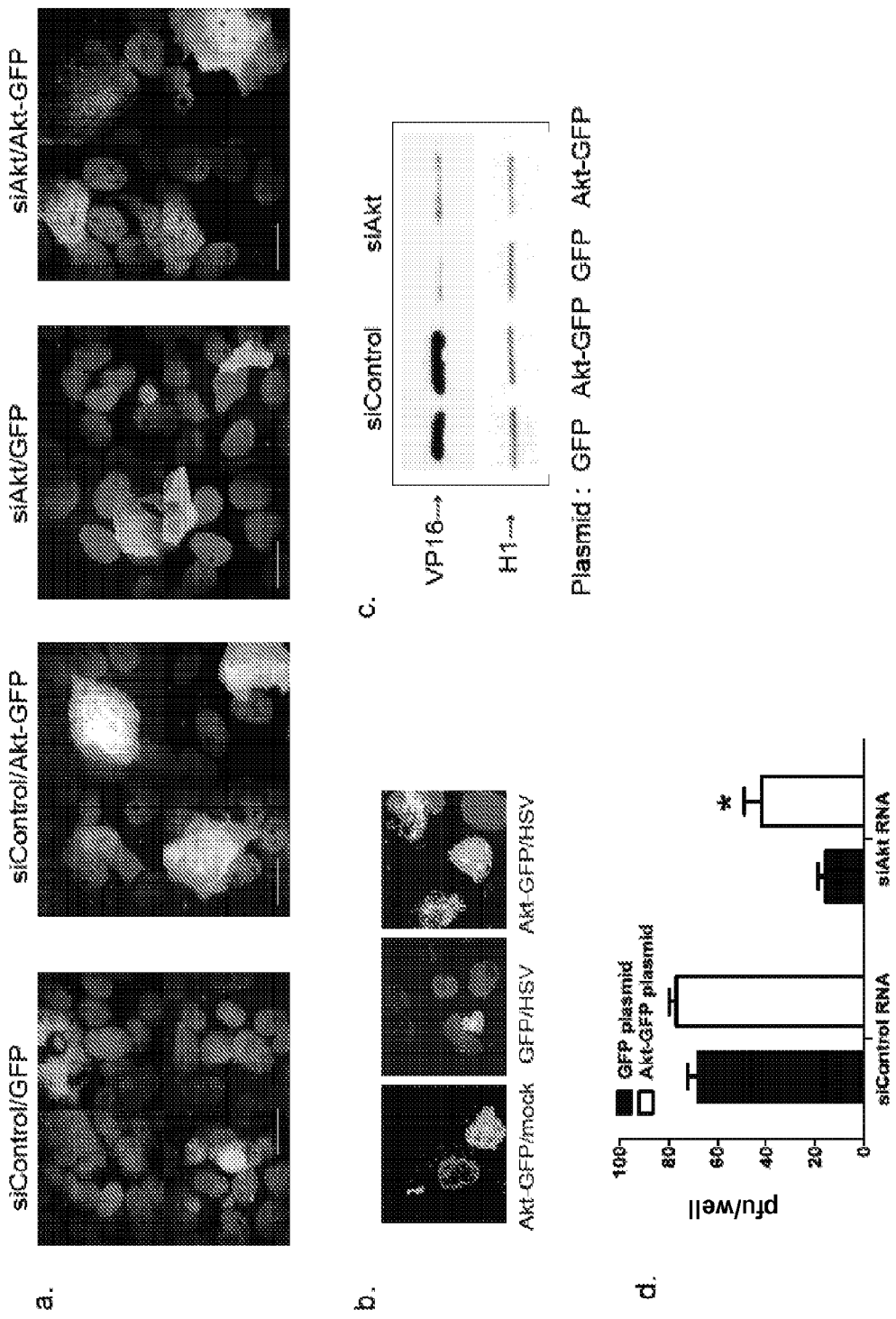
FIG. 5A-5D: Reintroducing Akt into silenced cells restores susceptibility to infection. Cells were transfected with siAkt1 or siControl and then 72 h later were transfected with a plasmid expressing Akt-GFP or GFP alone. Cells were fixed 72 h after plasmid transfection, immunostained with antibodies to Akt (red) (lighter gray in grayscale), nuclei stained with DAPI (blue) (darkest gray in grayscale) and analyzed by confocal microscopy. Images obtained from four independent fields are shown (a). Cells were transfected with siAkt and 72 h later transfected wither with GFP-Akt plasmid or plasmid containing GFP. The cells were then loaded with Calcium Crimson 48 h post introduction of the plasmids and mock-infected or infected with purified HSV-2(G). Live images were acquired 3 min post-temperature shift to 37° C. as in FIG. 5. The nuclei were stained blue with DAPI. Colocalization of $Ca^{2+}$ (red) and GFP-transfected cells (green) is yellow (lightest gray in grayscale). Representative images are shown (b). The transfected cells (siRNA followed by plasmid transfection) were inoculated with HSV-2(G) (moi ~1 pfu/cell) and nuclear extracts were prepared and analyzed for VP16 by Western blotting; blots were also probed for H1 as a control. Blots shown are representative of results obtained in 2 independent experiments (c). Silenced cells (siControl or siAkt) were transfected with the indicated plasmids (Akt-GFP or GFP) and then 72 h later, infected with HSV-2. Plaques were counted and results are presented as pfu/well and are means from 2 independent experiments performed in duplicate; the asterisk denotes significant increase in pfu in siAkt cells transfected with Akt-GFP plasmid compared to siAkt cells transfected with control plasmid (p=0.04) (d).

Introduction of a plasmid expressing Akt into silenced cells restores susceptibility to HSV infection. One of the limitations of siRNA is the possibility that results obtained could reflect off-target silencing. To address this possibility, Akt was reintroduced into siRNA-transfected cells. Cells were transfected with siAkt1 and then 72 h later, were transfected with a plasmid expressing an Akt1-GFP fusion protein or GFP alone. After 72 h in culture, confocal imaging and Western blots were performed to assess the efficiency of cellular Akt silencing and plasmid transfection. GFP was detected in 20-30% of cells (n=~100) transfected with either the Akt-GFP or control GFP plasmid (FIG. 5a). Native Akt (red) was detected in the majority of siControl cells in both the GFP+ (merge, yellow) and GFP-negative populations. In contrast, Akt was rarely detected in siAkt cells transfected with a control GFP plasmid, but was detected in the GFP+ cells following transfection with the Akt-GFP plasmid. There was partial restoration of susceptibility to infection in siAkt cells following transfection with the plasmid expressing Akt-GFP as evidenced by $Ca^{2+}$ response on live confocal imaging 5 minutes post-viral exposure ($Ca^{2+}$ detected with Calcium Crimson, red) (FIG. 5b), VP16 nuclear transport (FIG. 5c), and viral plaque assay (FIG. 5d).

Figure 6:
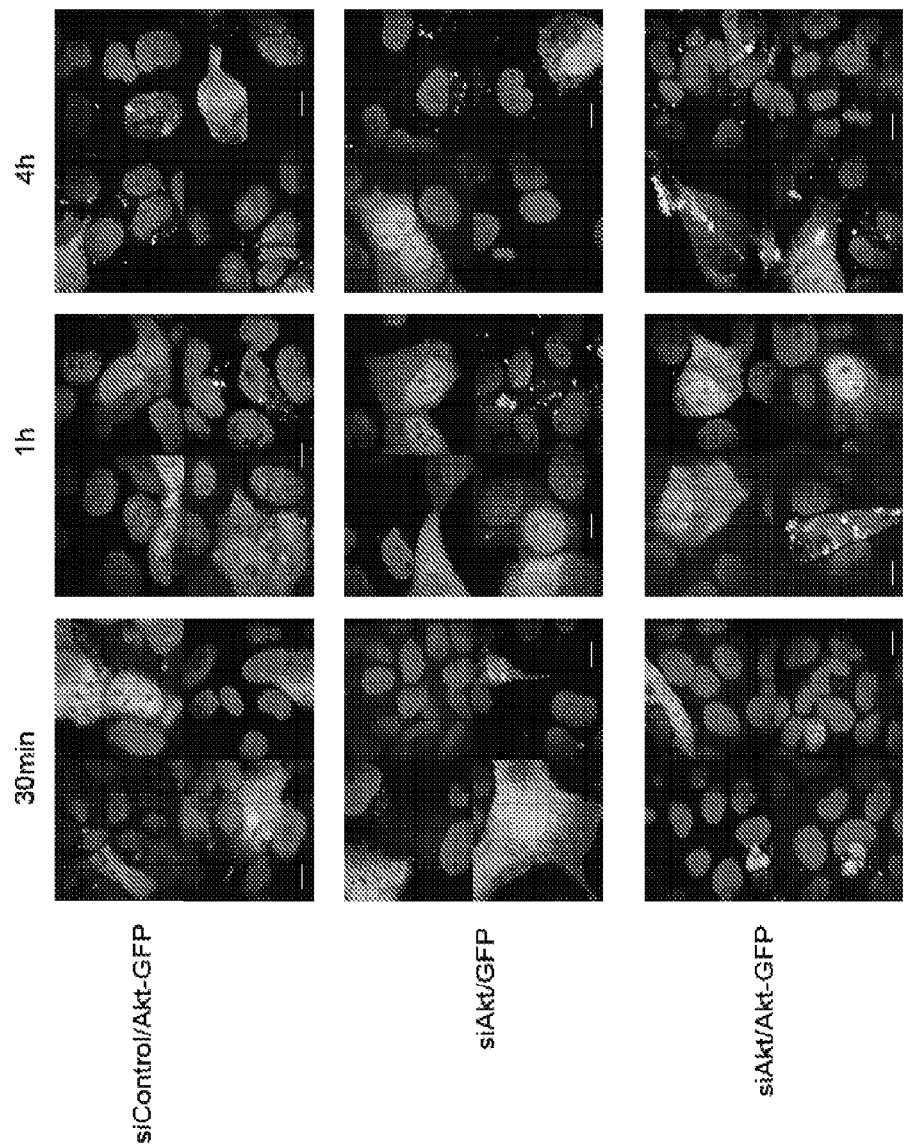
FIG. 6: Susceptibility to infection is restricted to cells expressing Akt. Transfected (siRNA followed by plasmid transfection with Akt-GFP or GFP alone) were exposed to purified HSV-F-GS2822 (capsids, red) (moi 1 pfu/cell) and then at the indicated times pi, cells were fixed with 4% of paraformaldehyde, nuclei stained with DAPI (blue) and confocal images acquired. Four independent fields are shown.

To determine whether the recovery of susceptibility to infection mapped to the cells expressing Akt, additional confocal studies were performed with an HSV-1 variant that expresses red fluorescent protein fused to VP16 (Antinone, 2010). Red capsids were detected in the majority of GFP+ and GFP-negative cells in siControl cells transfected with the Akt-GFP plasmid (FIG. 6, upper panel), but only in the GFP+ cells (merge, yellow) in siAkt cells transfected with the Akt-GFP plasmid (lower panel). Viral capsids were rarely detected in siAkt cells transfected with the control plasmid (middle panel). Together these findings indicate that the impediment to HSV entry in cells transfected with siAkt is attributable to the silencing of Akt and not an off-target effect.

Figures 7A, 7B, 7C, 7D:
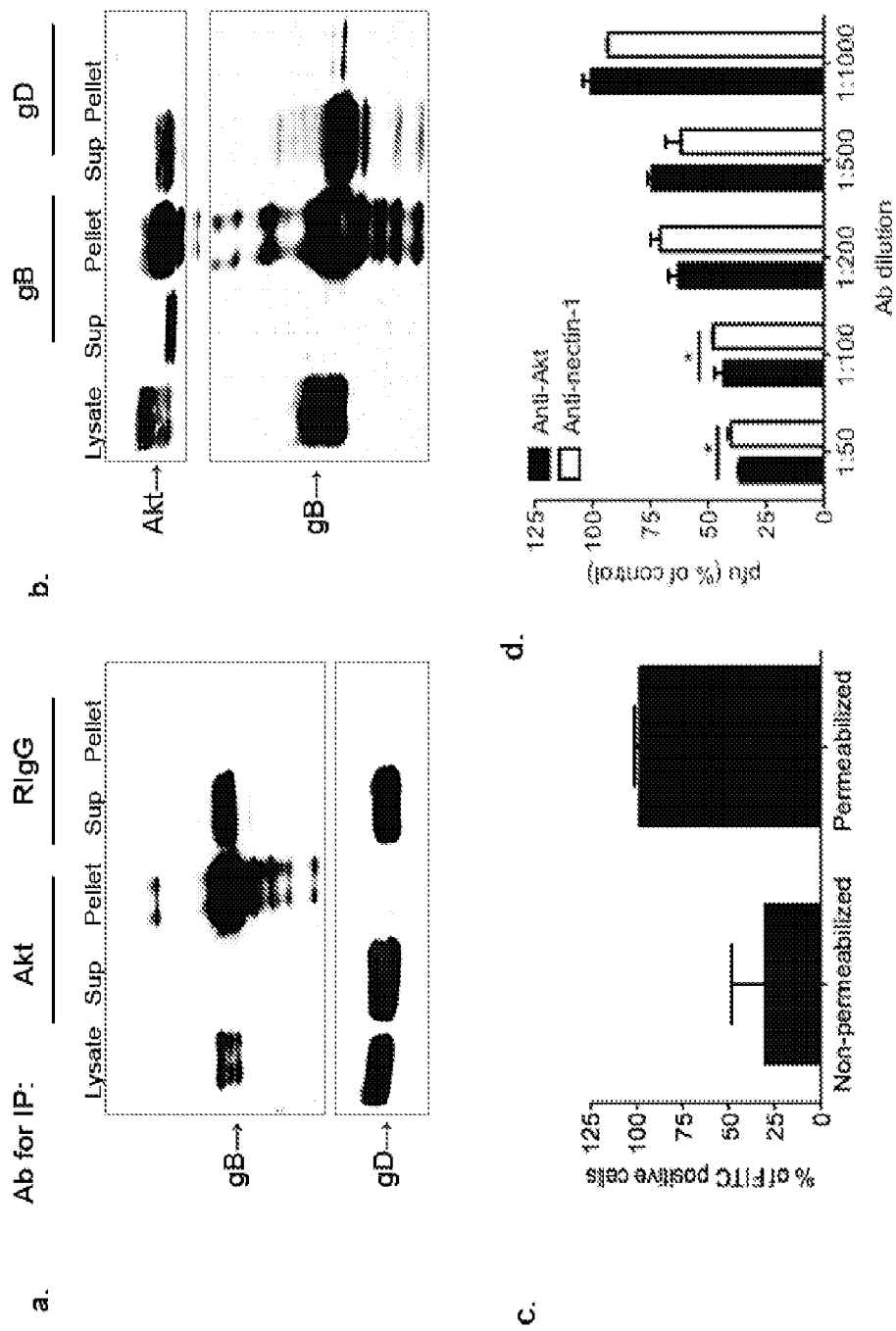
FIG. 7A-7D: Akt co-immunoprecipitates with glycoprotein B. CaSki cells were synchronously infected with purified HSV-2 (moi=10) and cell lysates were harvested 15 min post-temperature shift and incubated with rabbit polyclonal anti-Akt or a control rabbit polyclonal antibody (RIgG). The immune complexes were precipitated and an equivalent volume of cell lysates prior to precipitation, supernatant (sup) and pellet were subjected to Western blotting with anti-gB or anti-gD monoclonal antibodies (a) In reciprocal experiments, the lysates from HSV-infected cells were precipitated with anti-gB or anti-gD mAbs and analyzed by Western blotting with antibodies to Akt or gB (b). Uninfected CaSki cells were stained with FITC-conjugated anti-Akt antibodies either with or without permeabilization and Akt expression monitored by flow. Results are presented as % FITC positive cells in two independent experiments (c). CaSki cells were pretreated with anti-Akt, anti-nectin-1, or control rabbit IgG for 15 minutes prior to infection. After a 1 h incubation, cells were washed, overlaid with medium, and plaques were counted after 48 h incubation. Results are presented as percentage inhibition of pfu relative to controls wells and are means from two independent experiments conducted in duplicate (d). The asterisk indicates significant difference relative to control wells (p<0.05).

Akt interacts with glycoprotein B: To explore the possibility that Akt interacts directly with viral envelope glycoproteins, co-immunoprecipitation studies were performed. CaSki cells were synchronously infected with purified HSV-2 (moi 5 pfu/cell) by allowing virus to bind at 4° C. for 5 h, washing the cells to remove unbound virus, and then transferring the cultures to 37° C. to allow fusion to occur. Cell lysates were prepared 15 min after the shift in temperature and were incubated with a rabbit polyclonal antibody to Akt or a control rabbit IgG. The immune complexes were precipitated with Protein A-agarose and analyzed by Western blot with monoclonal antibodies to gB or gD (FIG. 7a). Glycoprotein B, but not gD, was detected in the pellet following precipitation with anti-Akt antibodies, but was retained in the supernatant when proteins were precipitated with a control antibody. Conversely, Akt was detected in the pellet following precipitation with anti-gB, but was retained in the supernatant when proteins were precipitated with anti-gD (FIG. 7b).

The observation that gB and Akt co-immunoprecipitate suggests that Akt must be accessible to viral envelope glycoproteins at the plasma membrane. Akt was detected in 30±18% of non-permeabilized uninfected cells and 98±3% of permeabilized cells by flow cytometry (FIG. 7c). Moreover, pretreatment of the cells with antibodies to Akt (or antibodies to nectin-1, the primary gD receptor as a positive control), inhibited viral infection (FIG. 7d).

Figure 10:
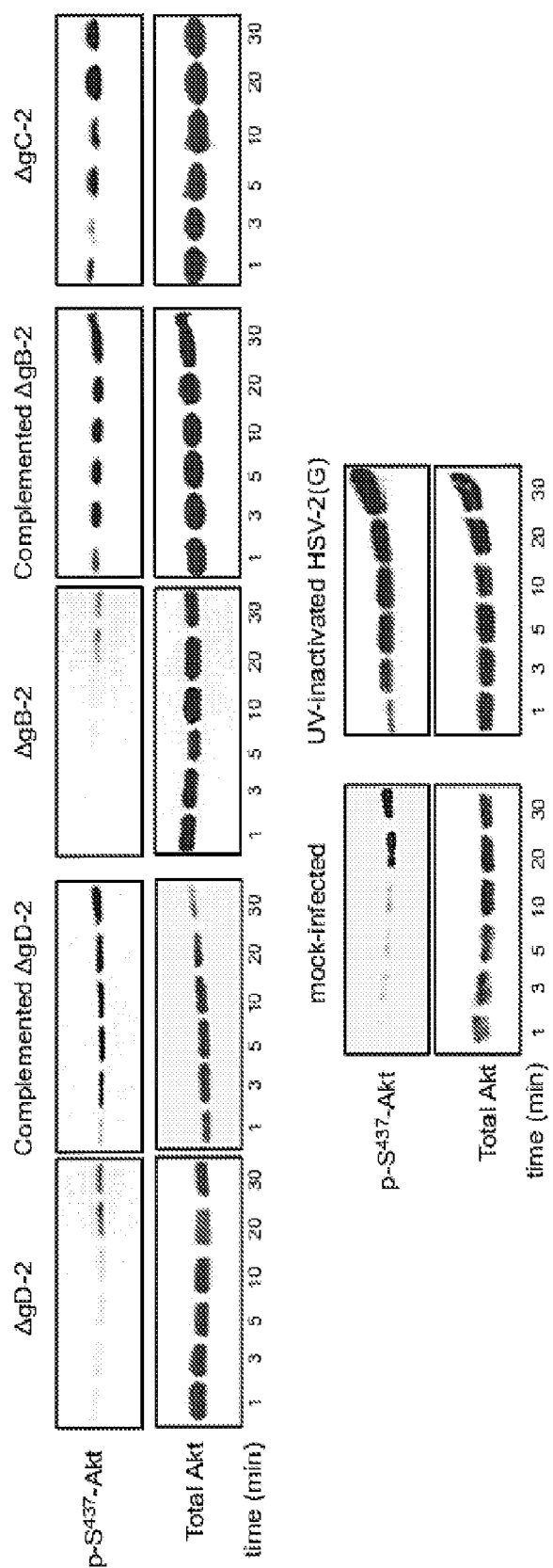
FIG. 10: Viruses deleted in HSV-2 gD and gB fail to trigger Akt phosphorylation. CaSki cells were serum starved for 24 h and then exposed to serum-free medium (mock-infection) or infected with ΔgD-2 grown on non-complementing or complementing cells, ΔgB-2 grown on non-complementing or complementing cells, ΔgC-2, or UV-inactivated HSV-2(G) (MOI 10 PFU/cell or equivalent number of particles for the ΔgD-2 and ΔgB-2 viruses), and cell lysates were prepared for Western blotting at the indicated times post-infection. Blots were incubated with anti-pS473-Akt123 and then stripped and probed with anti-total Akt123. Representative blots from ≤3 independent experiments are shown.

To explore whether the viral induced phosphorylation of Akt occurs in response to binding or entry, HSV-2 viruses impaired in binding (ΔgB-2) or entry ΔgD-2 were tested. Controls included the two deletion viruses grown on respective complementing cells, a gC-2-deletion virus, and UV-inactivated HSV-2(G); the latter are all competent for binding and entry. There was little or no increase in Akt phosphorylation in response to ΔgD-2 or ΔgB-2 viruses. In contrast, the complemented, ΔgC-2, and UV-inactivated viruses induced rapid phosphorylation of Akt (FIG. 10). Together, these studies indicate that binding alone is not sufficient to induce Akt phosphorylation and are consistent with the notion that gB and/or gD directly interacts with Akt.

Figures 8A, 8B:
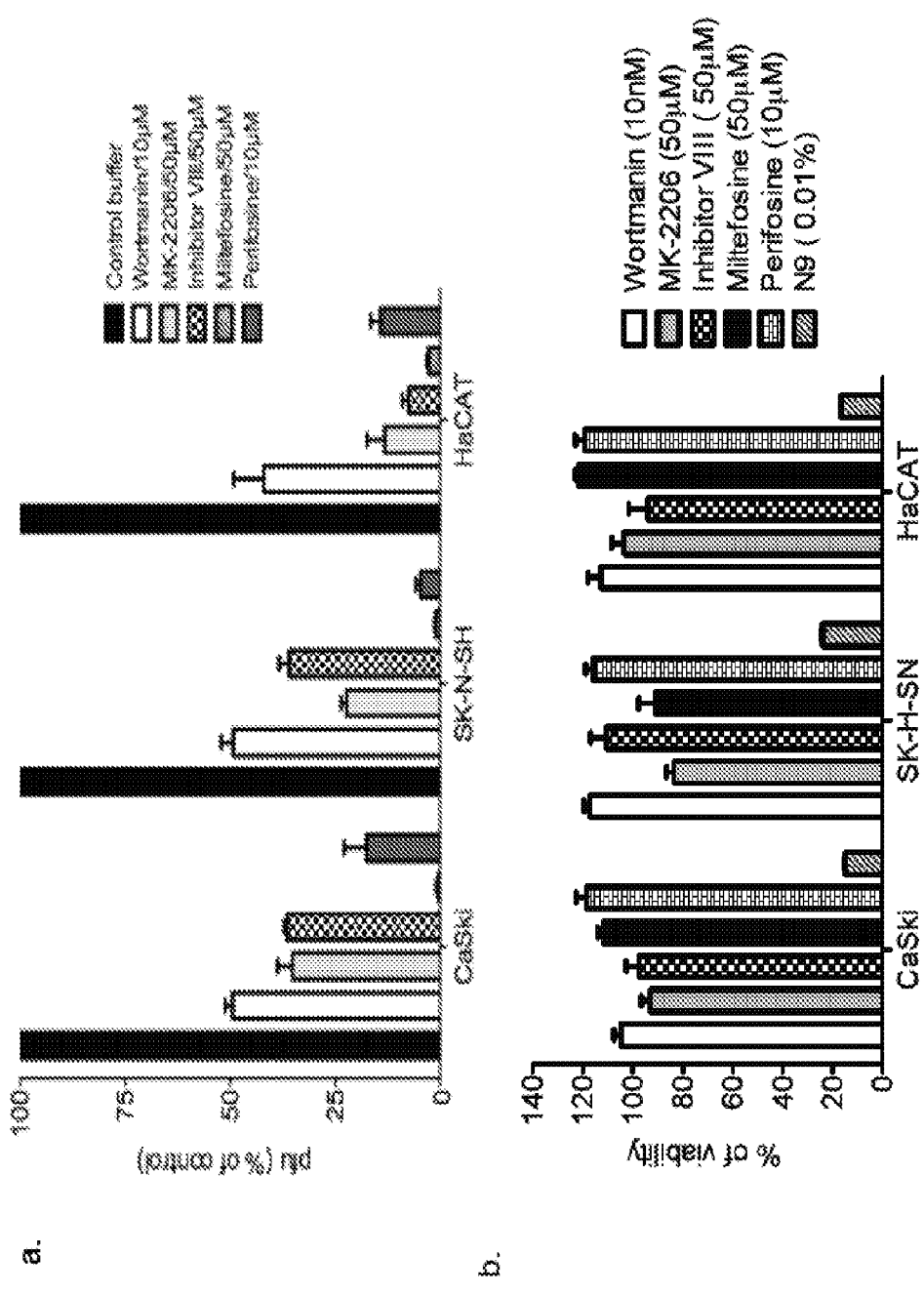
FIG. 8A-8B: Pharmacological inhibitors of Akt signaling inhibit HSV-2 plaque formation. Cells (CaSki, SK-N-SH, or HaCAT) cells were pretreated for 15 minutes with each of the indicated drugs and then challenged with serial dilutions of HSV-2. The inoculum (and drug) were removed after 1 h, and then cells were overlaid with fresh medium; plaques were counted after 48 h incubation. Results are presented as percent pfu relative to control wells (treated with 0.1% DMSO) (a). Alternatively, cells were treated for 24 h with drugs alone (0.01% nonoxynol-9 (N9) is included as a positive toxicity control) and then cell viability determined by MTT assay (b).

Akt is a potential target for HSV treatment: A series of Akt pharmacological inhibitors being developed as adjunct therapy for cancer including MK-2206, an allosteric Akt inhibitor (Yap, 2011); inhibitor VIII, which binds to the pleckstrin homology domain of Akt and prevents subsequent phosphorylation as well as translocation of Akt to the plasma membrane (Calleja, 2009); miltefosine, a drug licensed for treatment of leishmaniasis and other protozoal infections that blocks Akt phosphorylation (Ruiter, 2003), and perifosine, a structural analogue of miltefosine in Phase 3 clinical trials for treatment of several cancers (Richardson, 2012) were tested. Cells were pretreated with each drug for 15 min at the indicated concentrations and then infected with HSV-2 for 1 h. The inoculum was removed by washing and plaques were counted 48 h pi; toxicity assays were conducted in parallel using an MTT assay. All of the drugs inhibited HSV infection by variable amounts in each of the cell types at concentrations that were not cytotoxic (FIGS. 8a and b). However, miltefosine was the most potent.

Figures 9A, 9B, 9C, 9D:
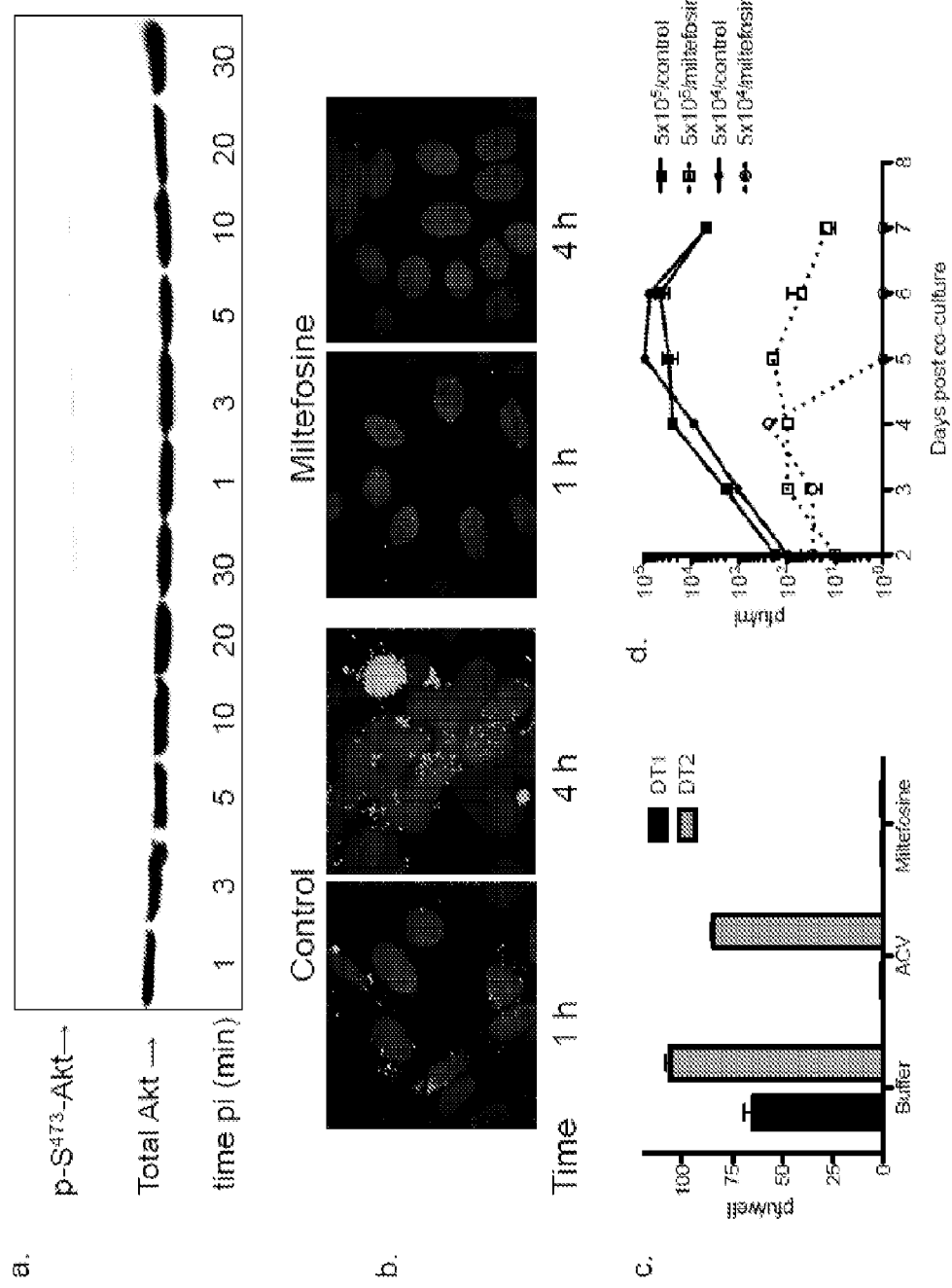
FIG. 9A-9D: Miltefosine prevents HSV induced Akt signaling, entry, infection by acyclovir-resistant and acyclovir susceptible clinical isolates and amplification of virus in a ganglion ex vivo co-culture model. HaCAT cells were pretreated with miltefosine and then exposed to serum free media (mock-infection) or infected with HSV-2(G) diluted in serum-free media (moi 10 pfu/cell) and cell lysates were prepared for Western blotting at the indicated times pi as described in FIG. 1. Blots were incubated with anti-pS473-Akt1/2/3 and anti-total Akt1/2/3 (a). CaSki cells were pretreated with control buffer (0.01% DMSO) or miltefosine and then exposed to purified HSV-1 K26GFP (viral capsids are green) (lightest gray in grayscale) and at the indicated times pi, cells were fixed and viewed by confocal microscopy; nuclei were stained with DAPI (blue) (darker gray in grayscale). Representative images are shown (b). CaSki cells were pretreated with control buffer or with miltefosine prior to Infection with an acyclovir susceptible (DT1) or acyclovir-resistant (DT2) isolate. Alternatively cells were pretreated with control buffer and acyclovir (dose) was added to the overlay media. Results are means of two independent experiments conducted in duplicate and are presented as percent inhibition of pfu relative to the control wells (c). Sacral ganglia were extracted from mice on day 7 following intravaginal infection with the indicated viral inoculum and co-cultured ex vivo with Vero cells in medium containing DMSO or 20 µM miltefosine. Culture supernatants were collected on the indicated days post-co-culture and viral growth monitored by plaque assay. Results are presented as pfu/ml (mean±sd) obtained from two independent experiments; each with sacral ganglia (d).

Subsequent studies with miltefosine demonstrated that the drug blocked viral induced phosphorylation of Akt (FIG. 9a), prevented viral induced $Ca^{2+}$ response (FIG. 4c) and prevented viral entry as indicated by confocal imaging with GFP labeled virus (FIG. 9b). Miltefosine was active against acyclovir susceptible and acyclovir resistant viruses in a plaque assay (FIG. 9c) and blocked viral amplification in a ganglion explant co-culture model. Sacral ganglia were removed from mice that had been vaginally infected with $5\times10^4$ or $5\times10^5$ pfu of HSV-2 on Day 7 and were then co-cultured with Vero cells in the absence or presence of 20 µM miltefosine. Media was removed on the indicated days post-co-culture and assayed for the presence of infectious virus by titering on Vero cells. Co-culturing of ganglia with Vero cells resulted in amplification of viral Infection, whereas there was little viral growth when ganglia were co-cultured with Vero cells in the presence of miltefosine (FIG. 9d).

Discussion

These studies demonstrate for the first time that Akt plays an important role in viral entry and link Akt activation to $Ca^{2+}$ signaling at the plasma membrane. Exposure of cervical epithelial cells, neuronal cells or keratinocytes to either serotype of HSV triggered Akt phosphorylation and silencing of Akt expression or pharmacological blockade of its phosphorylation blocked the viral-induced $Ca^{2+}$ response and prevented viral entry. Susceptibility to HSV entry was partially restored if Akt was reintroduced into siAkt-silenced cells by transfection with a plasmid expressing Akt or by independently triggering the release of intracellular $Ca^{2+}$ by treating the cells with ionomycin.

The co-immunoprecipitation studies suggest that Akt may interact with the viral envelope glycoprotein B at the plasma membrane, most likely as part of a complex with other cellular components. Consistent with this is the observation that Akt localizes to plasma membrane microdomains such as lipid rafts, which are key regulators of Akt signaling and are found on both the inner and outer leaflet of plasma membrane (Lasserre, 2008) (Gao, 2011 #1741). Notably, a prior study found that the ectodomain of gB (but not gD or its receptors, HVEM and nectin), associated with lipid rafts during viral entry (Bender, 2003 #616). The authors speculated that gB may interact with lipid raft components to activate cell signaling and promote viral entry. Crystallography studies demonstrate that gB possesses PH domains (Heldwein, 2006), which could interact with the PH domains of Akt directly or indirectly through PIP2 or PIP3, and promote Akt phosphorylation by celluluar kinases such as phosphoinositide-dependent kinase 1 (PDK1) and/or Akt autophosphorylation.

The link between Akt phosphorylation and release of a local plasma membrane $Ca^{2+}$ store and the subsequent release of IP3R-mediated cytosolic stores is consistent with studies demonstrating that Akt potentiates IP3R-mediated $Ca^{2+}$ release (Hwang, 2009 #1015; Koulen, 2008 #1020). However, it was previously found that the cytosolic $Ca^{2+}$ response was impaired when integrin$\alpha v \beta 3$ was silenced (Cheshenko, 2007) (Trepanier and Herold, unpublished). Possibly, Akt phosphorylation promotes integrin$\alpha v \beta 3$ signaling, which in turn, activates PLC resulting in the hydrolysis of PIP2 and generation of IP3. The initial release of $Ca^{2+}$ from the plasma membrane and subsequently from IP3R-dependent ER stores may provide a positive feedback loop to further stimulate the activity of IP3Rs. This $Ca^{2+}$-induced $Ca^{2+}$ release (CICR) mechanism enables $Ca^{2+}$ signals to be rapidly amplified and spread throughout the whole cell as observed in confocal images (spatial) and by fluorometry, which revealed several waves of $Ca^{2+}$ release of varying amplitude and duration over the first hour following infection (FIG. 4).

Importantly, Akt signaling plays a role in HSV entry into multiple cell types and by both serotypes, showing that targeting this interaction provides a novel strategy for HSV treatment or suppression. Several pharmacological inhibitors of Akt signaling were screened and it was found that miltefosine was the post potent and blocked viral entry and infection by acyclovir susceptible and acyclovir-resistant HSV strains at concentrations that were not cytotoxic to cells. No cytotoxicity was observed when cells were cultured in miltefosine for one week in the ganglion ex vivo co-culture model.

The findings in this study expand the understanding of the complex model of HSV entry, which likely reflects the requirement for several envelope glycoproteins and the ability of HSV to enter multiple cell types through diverse mechanisms. The current studies focused on CaSki cells in which virus enter by fusion of the viral envelope with the cell plasma membrane. CaSki cells were selected because cervical epithelial cells are an important target of infection for both serotypes, as highlighted by epidemiological studies indicating that HSV-1 is now a common cause of genital herpes infections (Roberts, 2003 #253). It is envisaged that virus attaches to heparan sulfate moieties on syndecan proteoglycans, which is mediated by glycoprotein C (HSV-1) or glycoprotein B (HSV-2) (a) (Herold, 1991; Cheshenko, 2002; Cheshenko, 2007). Subsequently, gD interacts with nectin-1 (HVEM, an alternative gD co-receptor, does not play a role in entry into CaSki cells (Cheshenko, 2010) (b) and then, perhaps in response to a conformational change induced by engagement of gD with its co-receptor (Carfi, 2002; Connolly, 2005), gB interacts with Akt and other cellular components within plasma membrane microdomains resulting in the phosphorylation of Akt (c). Akt activation, in turn, may induce the release of an intracellular $Ca^{2+}$ store near the membrane to initiate the fusion process (d). The release of plasma membrane $Ca^{2+}$ coupled with the activation of Akt may promote integrin$\alpha v \beta 3$ signaling (e), which is also required for the subsequent release of IP3R-ER $Ca^{2+}$ stores (f). These signaling events culminate in the intracellular delivery of viral capsids (g), which are subsequently transported to the nuclear pore along microtubules by a process that requires focal adhesion kinase (FAK) activation (h) (Cheshenko, 2005).

Materials and Methods

Cells and Viruses: CaSki (human cervical epithelial cell line) (ATCC CRL-1550) and Vero (ATCC CCL-81) cells were passaged in DMEM supplemented with 10% fetal bovine serum, SK-N-SH (human neuroblastoma cell line) (ATCC HTB11TM) cells were passaged in DMEM-F12 supplemented with 10% fetal bovine serum, HaCAT (human keratinocyte cell line) (CLS 300493) cells were propagated in DMEM supplemented with 10% fetal bovine serum, and End1/E6E7 cells (gift from R. N. Fichorova and D. Anderson) were propagated in keratinocyte media supplemented with bovine pituitary extract and human recombinant EGF (Fichorova, 1997). The laboratory isolates HSV-2(G), HSV-1 (KOS), HSV-1(KVP26GFP), which contains a green fluorescent protein (GFP)-VP26 fusion protein (Desai, 1998 #176), and HSV-1 F-GS2822, which encodes the red fluorescent protein 1 fused to the N terminus of VP26 (Antinone, 2010) (gift from Greg Smith, Northwestern University), were propagated on Vero cells and viral stocks were stored at $-80°$ C. The HSV-2 clinical isolates 4674, DT1 (acyclovir susceptible) and DT2 (acyclovir resistant) were propagated on CaSki cells (Segarra, 2011)(Oram, 2000).

siRNA, plasmids and transfections: CaSki were transfected with each indicated siRNA sequence (final concentration 10 nM) in 12 well plates. The transfections were performed with the Effectene transfection reagent (Qiagen, Calif.) using the protocol provided by the manufacturer. The human Akt1 siRNA (633), Akt2 siRNA (103305), Akt3 siRNA (110901) and control siRNA (AM4636) were purchased from Applied Biosystems (Applied Biosystems, Foster City, Calif.). To reintroduce Akt, siRNA treated cells were transfected with 0.3 µg of pCMV-AC-GFP plasmid expressing Akt1 fused to GFP (RG201850, OriGene, Rockville, Md.) or a control plasmid expressing only GFP (pS100010, OriGene). Transfections with plasmids were performed 72 h after the introduction of siRNA.

Viral labeling and purification: Vero cells were infected with GFP labeled virus (~0.001 pfu/cell) and after 48 h, the infected cells were lysed and, if indicated, incubated with the lypophilic tracer DiI (1 µM) (Molecular Probes) for 10 min at room temperature before purification on sucrose gradients as previously described (Cheshenko, 2007). Titers of the purified viruses were determined by plaque assays.

Western blots: CaSki cells were harvested and lysed in 100 µl of buffer containing 20 mM Tris pH 7.5, 50 mM NaCl, 1% NP-40, 0.05% DOC, supplemented with fresh protease and phosphatase inhibitors. Proteins were separated by SDS-PAGE and transferred to membranes for immunoblotting with the indicated antibodies; membranes were stripped between antibodies. Blots were scanned and the band intensities were analyzed using GelDoc2000 system.

Antibodies and chemical reagents: Primary antibodies and dilutions for Western blot and confocal microscopy were as follows: mouse anti-anti-VP16 mAb, 1:500 (sc7545, Santa Cruz Biotechnology, Santa Cruz, Calif.); anti-gB mAb, 1:500 (sc-69799 Santa Cruz); anti-gD mAb, 1:1000 (sc-56988, Santa Cruz); anti-β-actin mAb, 1:5000 (A-5441, Sigma-Aldrich, St. Louis, Mo.); anti-phospho-Akt (ser 473) mAb, 1:500 (4051, Cell Signaling Technology Inc., Danvers, Mass.); anti-Akt1 mAb, 1:500 (sc-55523, Santa Cruz); anti-Histone H1 mAb, 1:250 (sc-8030, Santa Cruz) anti-nectin 1 mAb (CK 6,sc-21722, Santa Cruz); rabbit anti-total Akt1/2/3, 1:1000 (sc-8312, Santa Cruz); and rabbit anti-goat IgG, 1:500 (HAF017, R&D, Minneapolis, Minn.). The secondary antibodies for Western blots were horseradish peroxidase-conjugated goat anti-mouse (170-5047, Bio-Rad, Hercules, Calif.), goat anti-rabbit (170-5046, Bio-Rad). The secondary antibodies for confocal microscopy were anti-mouse Alexa 488, Alexa 555, or Alexa 350 and anti-rabbit Alexa 488 or Alexa 350 (A11001, A211422, A11045, A11008, A21068, Invitrogen Molecular Probes). All secondary antibodies were diluted 1:1000.

Stauroporine (PHZ1271) and ionomycin (124222) were purchased from Invitrogen Molecular Probes and wortmannin from TOCRIS (1232, Bristol, UK), miltefosine was purchased from Santa Cruz Biotechnology (sc-203135), perifosine and MK-2206 were purchased from Selleck Chemicals (s1037 and s1078, Houston, Tex.), and inhibitor VIII was purchased from Calbiochem (124018, EMD Millipore, Billerica, Mass.).

Viral binding, entry and plaque assays: For binding studies, cells were exposed to serial dilutions of purified virus for 5 h at 4° C. Unbound virus was removed by washing, and the cell-bound virus analyzed by preparing Western blots of cell lysates and probing with anti-gD mAb (1103, Virusys, Sykesville, Md.) (Cheshenko, 2002). For plaque assays, cells were exposed to serial dilutions of virus for 1 h and then washed three times with phosphate buffered saline (PBS), pH 7.4, and overlaid with 199 medium containing 1% pooled human IgG. Plaques were counted by immunoassay using an anti-human IgG antibody peroxidase conjugate (Calbiochem) (Herold, 1991). In select experiments cells were pretreated with drugs that block Akt signaling or acyclovir was added to the overlay medium. In other experiments, cells were pretreated with rabbit anti-total Akt1/2/3, anti-nectin 1 mAb, or control rabbit IgG for 15 min prior to infection. The ability of VP16, a viral tegument protein, to translocate to the nucleus following infection was assessed as a marker of viral entry. CaSki cells were infected at 37° C. for 45 min. with the indicated moi of virus, cells were then washed three times with PBS, overlaid with fresh media and nuclear extracts were prepared 45 min. later and analyzed by Western blot for VP16 and histone H1 (Cheshenko, 2003).

Confocal microscopy: Viral entry was also monitored by confocal microscopy. Cells were grown on glass coverslips in 12-well plates, transfected with the indicated siRNA and 48 h post-transfections, infected with DiI-labeled HSV-1 (KVP26GFP). To label plasma membranes, the cells were stained for 30 min with EZ-Link sulfosuccinimidobiotin (EZ-Link) reagent (0.1 mM; Pierce Chemical, Rockford, Ill.), which reacts with primary amines on cell-surface proteins before infection, fixed with 4% paraformaldehyde solution (Electron Microscopy, Hatfield, Pa.) at the indicated times pi, and the biotinylated cells were reacted with Alexa Fluor 350-conjugated streptavidin (1:1000 dilution; 511225, 511249; Invitrogen, Carlsbad, Calif.). Images were acquired by laser confocal microscope ZeissLive/DuoScan equipped with an oil immersion objective 100×1.4. Images were captured in an optical slice of ~0.5 μm with appropriate filters, Alexa Fluor 488, and GFP were excited using the 488-nm line of a krypton/argon laser and viewed with a 505- to 530-nm band pass μm. AlexaFluor 360 were excited with 405-nm diode laser and collected with 420 to 475 nm filter, AlexaFluor 555 were excited using 561-nm helium/neon laser and collected with a 575 to 655 filter. All images were captured using the multi-track mode of the microscope to decrease cross talk of fluorescent signals. Z-sections were captured in an optical slice of 0.5 μm and 15-20 cells were scanned per experiment.

Calcium live image microscopy: Cells were grown in glass bottom culture dishes 35 mm (P35G-1.5-10-C; MatTek corporation, Ashland, Mass.) and labeled with Image-iT TM LIVE Intracellular Membrane and Nuclear labeling Kit (134407; Invitrogen). The cells were then loaded with Calcium Green or Calcium Crimson (C-3012,C-3018, 2.5 μg/ml, Invitrogen) for 4 h at 4° C., and infected with purified virus for 4 h at 4° C. Cells were washed three times with PBS to remove extracellular $Ca^{2+}$ and unbound virus, overlaid with 25 mM HEPES buffer, and placed into a temperature-regulated 37° C. environmental chamber in a ZeissLive/DuoScan confocal microscope fitted with a 100×1.4 oil objective. Images were acquired 3 min after the dishes were placed in the chamber. Image analysis was conducted using the LSM confocal software package (Carl Zeiss, Inc.) and quantification of intensity staining with image J software (National Institutes of Health, Bethesda, Md.). Three-dimensional (3-D) images were generated using the Volocity 4 confocal software (Improvision, Lexington, Mass.).

Calcium kinetic measurements: CaSki cells ($5 \times 10^4$) were seeded in 96 well black plates with clear bottoms (3340, Ce11BIND surface, Corning Inc., NY) and incubated with 25 μM Fura-2/AM diluted in PBS (F1221, Invitrogen Molecular Probes) for 60 min at 37° C., rinsed with PBS thrice, placed on ice and then exposed to cold purified HSV-2 (moi ~5 pfu/cell) or control buffer (PBS). In select experiments, cells were pretreated with 5 nM wortmannin prior to infection. Additional controls included cells exposed to 1 μM of ionomycin. The cells were then transferred to SpectraMaxMFe temperature-regulated chamber at 37° C. (Molecular Devices Ca) without washing; photometric data for [$Ca^{2+}$] were generated by exciting cells at 340 and 380 nm and measuring emission at 510 nm every minute for one hour. An intracellular calibration was performed with each experiment by determining the fluorescence ratio (340:380) in the presence of Ca-free 10 mM K2EGTA buffer (Rmin) and 10 mM CaEGTA buffer containing 10 μM ionomycin (Rmax) (C-3008, Calcium Calibration Buffer Kit #1, Invitrogen Molecular Probes). The mean [$Ca^{2+}$] was determined from four wells according to the manufacturer's recommendations using the following equation: [$Ca^{2+}$]=Kd Q (R−Rmin)/(R max−R), where R represents the fluorescence intensity ratio Fλ1/Fλ2; λ1 (340 nm) and λ2 (380 nm) are the fluorescence detection wavelengths for ion-bound and ion-free indicators; Kd is the $Ca^{2+}$ dissociation constant and equals 0.14 μM (Fura and Indo Ratiometric Calcium Indicators, Invitrogen Molecular Probes); and Q is the ratio of Fmin to Fmax at λ2 (380 nm).

Immunoprecipitation assay: Cells were serum-starved for 24 h prior to being synchronously infected with purified HSV-2 (moi 0.5 or 5 pfu/cell) and 15 minutes pi, cells were lysed by sonication in RIPA buffer (Thermo Scientific) supplemented with complete protease inhibitors (Roche Diagnostics). The lysates were incubated with equal amount (based on protein concentration provided by manufacture) of rabbit polyclonal anti-Akt or control rabbit IgG (sc-2763, Santa Cruz) overnight at 4° C. and then immune complexes were isolated following a 2-h incubation with Protein A agarose beads (Thermo Scientific). The precipitated complexes (pellet), supernatants or an aliquot of the non-immunoprecipitated cell lysate were analyzed by Western blot for gB or gD. Reciprocal immunoprecipitation studies were performed by immunoprecipitating lysates from infected cells with anti-gB (sc-52425, Santa Cruz) or anti-gD (sc-21719, Santa Cruz) mAbs and probing for gB and Akt by Western blot.

Toxicity assays: CaSki cells were transfected and grown in 96-well plates and cell viability was determined 72 h after transfection using a cell proliferation assay (CellTiter96; Promega Calif., USA). Controls included cells exposed to media alone or exposed to 0.01% N-9. Optical density was determined using a Beckman Coulter DTX880 multi-detection microplate reader. To determine if transfections induced apoptosis, CaSki cells were transfected for 72 h and either mock treated or incubated with 1 μM stauroporine (EMD Chemicals, Gibbstown, N.J.) for 4 h, then fixed in 4% paraformaldehyde and permeabilized in 1% Triton-X. The cells were stained with the Click-iT TUNEL Alexa Fluor 594 (C10246, Invitrogen Molecular Probes). The percentage of cell death was determined by quantifying a total of 100 cells visualized in 4 random fields.

Flow cytometry. CaSki cells were stained with anti-Akt FITC (1:50, sc-5298, Santa Cruz Biotechnology) for 20 min at room temperature, washed 3 times and then fixed for 20 min with fixative buffer (554855, BD Cytofix, BD Bioscience Pharmagen San Diego, Ca). Alternatively the cells were first fixed and pemeablized (51-2090KZ, BD Cytofix/Cytoperm Fixation/permebealization Kit, BD Biosciences Pharmagen) for 20 min, then washed 3 times and stained with anti-Akt FITC for 20 min at room temperature. Cells were analyzed by Becton Dickinson LSRII Flow cytometer and data were processed by Flow Jo software.

Ganglion-epithelial cell ex vivo co-cultures: Seven days pi, sacaral ganglia were excised from animals that been intravaginally infected with $5\times10^4$ or $5\times10^5$ pfu of HSV-2(4674). The tissue was co-cultured with confluent Vero cells in 60-mm Petri dishes containing DMEM supplemented with 0.1% DMSO (control) or with 20 μM of miltefosine. Culture supernatants were collected on days 2-7 post-co-culture and concentration of virus released into the media determined by plaque assay on Vero cells.

REFERENCES

Alessi, D. R., S. R. James, C. P. Downes, A. B. Holmes, P. R. Gaffney, C. B. Reese, and P. Cohen. 1997. Characterization of a 3-phosphoinositide-dependent protein kinase which phosphorylates and activates protein kinase Balpha. *Curr Biol* 7:261-269.

Antinone, S. E., and G. A. Smith. 2010. Retrograde axon transport of herpes simplex virus and pseudorabies virus: a live-cell comparative analysis. *J Virol* 84:1504-1512.

Belshe, R. B., P. A. Leone, D. I. Bernstein, A. Wald, M. J. Levin, J. T. Stapleton, I. Gorfinkel, R. L. Morrow, M. G. Ewell, A. Stokes-Riner, G. Dubin, T. C. Heineman, J. M. Schulte, and C. D. Deal. 2012. Efficacy results of a trial of a herpes simplex vaccine. *N Engl J Med* 366:34-43.

Bender, F. C., J. C. Whitbeck, M. Ponce de Leon, H. Lou, R. J. Eisenberg, and G. H. Cohen. 2003. Specific association of glycoprotein B with lipid rafts during herpes simplex virus entry. *J Virol* 77:9542-9552.

Benetti, L., and B. Roizman. 2006. Protein kinase B/Akt is present in activated form throughout the entire replicative cycle of deltaU(S)3 mutant virus but only at early times after infection with wild-type herpes simplex virus 1. *J Virol* 80:3341-3348.

Berridge, M. J. 2009. Inositol trisphosphate and calcium signalling mechanisms. *Biochim Biophys Acta* 1793:933-940.

Calleja, V., M. Laguerre, P. J. Parker, and B. Larijani. 2009. Role of a novel PH-kinase domain interface in PKB/Akt regulation: structural mechanism for allosteric inhibition. *PLoS Biol* 7:e17.

Carfi, A., H. Gong, H. Lou, S. H. Willis, G. H. Cohen, R. J. Eisenberg, and D. C. Wiley. 2002. Crystallization and preliminary diffraction studies of the ectodomain of the envelope glycoprotein D from herpes simplex virus 1 alone and in complex with the ectodomain of the human receptor HveA. *Acta Crystallogr D Biol Crystallogr* 58:836-838.

Cheshenko, N., B. Del Rosario, C. Woda, D. Marcellino, L. M. Satlin, and B. C. Herold. 2003. Herpes simplex virus triggers activation of calcium-signaling pathways. *J Cell Biol* 163:283-293.

Cheshenko, N., and B. C. Herold. 2002. Glycoprotein B plays a predominant role in mediating herpes simplex virus type 2 attachment and is required for entry and cell-to-cell spread. *J Gen Virol* 83:2247-2255.

Cheshenko, N., W. Liu, L. M. Satlin, and B. C. Herold. 2005. Focal adhesion kinase plays a pivotal role in herpes simplex virus entry. *J Biol Chem* 280:31116-31125.

Cheshenko, N., W. Liu, L. M. Satlin, and B. C. Herold. 2007. Multiple receptor interactions trigger release of membrane and intracellular calcium stores critical for herpes simplex virus entry. *Mol Biol Cell* 18:3119-3130.

Cheshenko, N., J. B. Trepanier, T. J. Segarra, A. O. Fuller, and B. C. Herold. 2010. HSV usurps eukaryotic initiation factor 3 subunit M for viral protein translation: novel prevention target. *PLoS One* 5:e11829.

Chugh, P., B. Bradel-Tretheway, C. M. Monteiro-Filho, V. Planelles, S. B. Maggirwar, S. Dewhurst, and B. Kim. 2008. Akt inhibitors as an HIV-1 infected macrophage-specific anti-viral therapy. *Retrovirology* 5:11.

Connolly, S. A., D. J. Landsburg, A. Carfi, J. C. Whitbeck, Y. Zuo, D. C. Wiley, G. H. Cohen, and R. J. Eisenberg. 2005. Potential nectin-1 binding site on herpes simplex virus glycoprotein d. *J Virol* 79:1282-1295.

Corey, L., A. Wald, R. Patel, S. L. Sacks, S. K. Tyring, T. Warren, J. M. Douglas, Jr., J. Paavonen, R. A. Morrow, K. R. Beutner, L. S. Stratchounsky, G. Mertz, O. N. Keene, H. A. Watson, D. Tait, and M. Vargas-Cortes. 2004. Once-daily valacyclovir to reduce the risk of transmission of genital herpes. *N Engl J Med* 350:11-20.

Desai, P., and S. Person. 1998. Incorporation of the green fluorescent protein into the herpes simplex virus type 1 capsid. *J Virol* 72:7563-7568.

Fichorova, R. N., and D. J. Anderson. 1999. Differential expression of immunobiological mediators by immortalized human cervical and vaginal epithelial cells. *Biol Reprod* 60:508-514.

Fichorova, R. N., J. G. Rheinwald, and D. J. Anderson. 1997. Generation of papillomavirus-immortalized cell lines from normal human ectocervical, endocervical, and vaginal epithelium that maintain expression of tissue-specific differentiation proteins. *Biol Reprod* 57:847-855.

Gao, X., P. R. Lowry, X. Zhou, C. Depry, Z. Wei, G. W. Wong, and J. Zhang. 2011. PI3K/Akt signaling requires spatial compartmentalization in plasma membrane microdomains. *Proc Natl Acad Sci USA* 108:14509-14514.

Garg, R., and M. J. Tremblay. 2012. Miltefosine represses HIV-1 replication in human dendritic cell/T-cell cocultures partially by inducing secretion of type-I interferon. *Virology*

Harlan, J. E., P. J. Hajduk, H. S. Yoon, and S. W. Fesik. 1994. Pleckstrin homology domains bind to phosphatidylinositol-4,5-bisphosphate. Nature 371:168-170.

Heldwein, E. E., and C. Krummenacher. 2008. Entry of herpesviruses into mammalian cells. *Cell Mol Life Sci* 65:1653-1668.

Heldwein, E. E., H. Lou, F. C. Bender, G. H. Cohen, R. J. Eisenberg, and S. C. Harrison. 2006. Crystal structure of glycoprotein B from herpes simplex virus 1. Science 313:217-220.

Herold, B. C., D. WuDunn, N. Soltys, and P. G. Spear. 1991. Glycoprotein C of herpes simplex virus type 1 plays a principal role in the adsorption of virus to cells and in infectivity. *J Virol* 65:1090-1098.

Hwang, J. Y., R. S. Duncan, C. Madry, M. Singh, and P. Koulen. 2009. Progesterone potentiates calcium release through IP3 receptors by an Akt-mediated mechanism in hippocampal neurons. *Cell Calcium* 45:233-242.

Jha, T. K., S. Sundar, C. P. Thakur, P. Bachmann, J. Karbwang, C. Fischer, A. Voss, and J. Berman. 1999. Miltefosine, an oral agent, for the treatment of Indian visceral leishmaniasis. *N Engl J Med* 341:1795-1800.

Koulen, P., C. Madry, R. S. Duncan, J. Y. Hwang, E. Nixon, N. McClung, E. V. Gregg, and M. Singh. 2008. Progesterone potentiates IP(3)-mediated calcium signaling through Akt/PKB. *Cell Physiol Biochem* 21:161-172.

Lakadamyali, M., M. J. Rust, H. P. Babcock, and X. Zhuang. 2003. Visualizing infection of individual influenza viruses. *Proc Natl Acad Sci USA* 100:9280-9285.

Lasserre, R., X. J. Guo, F. Conchonaud, Y. Hamon, O. Hawchar, A. M. Bernard, S. M. Soudja, P. F. Lenne, H. Rigneault, D. Olive, G. Bismuth, J. A. Nunes, B. Payrastre, D. Marguet, and H. T. He. 2008. Raft nanodomains contribute to Akt/PKB plasma membrane recruitment and activation. *Nat Chem Biol* 4:538-547.

McManus, E. J., B. J. Collins, P. R. Ashby, A. R. Prescott, V. Murray-Tait, L. J. Armit, J. S. Arthur, and D. R. Alessi. 2004. The in vivo role of PtdIns(3,4,5)P3 binding to PDK1 PH domain defined by knockin mutation. *EMBO J* 23:2071-2082.

Oram, R. J., D. Marcellino, D. Strauss, E. Gustafson, C. L. Talarico, A. K. Root, P. L. Sharma, K. Thompson, J. D. Fingeroth, C. Crumpacker, and B. C. Herold. 2000. Characterization of an acyclovir-resistant herpes simplex virus type 2 strain isolated from a premature neonate. *J Infect Dis* 181:1458-1461.

Patterson, R. L., D. B. van Rossum, A. I. Kaplin, R. K. Barrow, and S. H. Snyder. 2005. Inositol 1,4,5-trisphosphate receptor/GAPDH complex augments Ca2+ release via locally derived NADH. *Proc Natl Acad Sci USA* 102:1357-1359.

Richardson, P. G., C. Eng, J. Kolesar, T. Hideshima, and K. C. Anderson. 2012. Perifosine, an oral, anti-cancer agent and inhibitor of the Akt pathway: mechanistic actions, pharmacodynamics, pharmacokinetics, and clinical activity. *Expert Opin Drug Metab Toxicol* 8:623-633.

Roberts, C. M., J. R. Pfister, and S. J. Spear. 2003. Increasing proportion of herpes simplex virus type 1 as a cause of genital herpes infection in college students. *Sex Transm Dis* 30:797-800.

Ruiter, G. A., S. F. Zerp, H. Bartelink, W. J. van Blitterswijk, and M. Verheij. 2003. Anti-cancer alkyl-lysophospholipids inhibit the phosphatidylinositol 3-kinase-Akt/PKB survival pathway. *Anticancer Drugs* 14:167-173.

Segarra, T. J., E. Fakioglu, N. Cheshenko, S. S. Wilson, P. M. Mesquita, G. F. Doncel, and B. C. Herold. 2011. Bridging the gap between preclinical and clinical microbicide trials: blind evaluation of candidate gels in murine models of efficacy and safety. *PLoS One* 6:e27675.

Sindermann, H., K. R. Engel, C. Fischer, and W. Bommer. 2004. Oral miltefosine for leishmaniasis in immunocompromised patients: compassionate use in 39 patients with HIV infection. *Clin Infect Dis* 39:1520-1523.

Soto, J., B. A. Arana, J. Toledo, N. Rizzo, J. C. Vega, A. Diaz, M. Luz, P. Gutierrez, M. Arboleda, J. D. Berman, K. Junge, J. Engel, and H. Sindermann. 2004. Miltefosine for new world cutaneous leishmaniasis. *Clin Infect Dis* 38:1266-1272.

Spear, P. G. 2004. Herpes simplex virus: receptors and ligands for cell entry. *Cell Microbiol* 6:401-410.

Testa, J. R., and A. Bellacosa. 2001. AKT plays a central role in tumorigenesis. *Proc Natl Acad Sci USA* 98:10983-10985.

Toker, A., and A. C. Newton. 2000. Akt/protein kinase B is regulated by autophosphorylation at the hypothetical PDK-2 site. *J Biol Chem* 275:8271-8274.

Tronstein, E., C. Johnston, M. L. Huang, S. Selke, A. Magaret, T. Warren, L. Corey, and A. Wald. 2011. Genital shedding of herpes simplex virus among symptomatic and asymptomatic persons with HSV-2 infection. *JAMA* 305:1441-1449.

Venkatachalam, K., D. B. van Rossum, R. L. Patterson, H. T. Ma, and D. L. Gill. 2002. The cellular and molecular basis of store-operated calcium entry. *Nat Cell Biol* 4:E263-272.

Wilson, S. S., E. Fakioglu, and B. C. Herold. 2009. Novel approaches in fighting herpes simplex virus infections. *Expert Rev Anti Infect Ther* 7:559-568.

Yap, T. A., L. Yan, A. Patnaik, I. Fearen, D. Olmos, K. Papadopoulos, R. D. Baird, L. Delgado, A. Taylor, L. Lupinacci, R. Riisnaes, L. L. Pope, S. P. Heaton, G. Thomas, M. D. Garrett, D. M. Sullivan, J. S. de Bono, and A. W. Tolcher. 2011. First-in-man clinical trial of the oral pan-AKT inhibitor MK-2206 in patients with advanced solid tumors. *J Clin Oncol* 29:4688-4695.

What is claimed:

1. A method of reducing the extent of a herpesvirus infection of a subject, comprising prophylactically administering to the subject an amount of an inhibitor of Akt effective to reduce the extent of a herpesvirus infection in a subject.

2. The method of any of claim 1, wherein the herpesvirus is a herpes simplex virus, a cytomegalovirus, an Epstein Barr virus, a human herpesvirus-6, a human herpesvirus-7, a Varicella zoster virus, or a Kaposi's sarcoma-associated herpesvirus.

3. The method of claim 1, wherein the herpesvirus is a herpes simplex virus-1 or is herpes simplex virus-2.

4. The method of claim 1, wherein the subject has neonatal encephalitis, sporadic encephalitis, and/or genital ulcerative disease.

5. The method of claim 1, wherein the subject is at risk of neonatal encephalitis or of sporadic encephalitis.

6. The method of claim 1, wherein the subject has a herpesvirus infection that is resistant to acyclovir and/or valacyclovir.

7. The method of claim 1, wherein the subject has neurological symptoms from a herpesvirus infection.

8. The method of claim 1, wherein the subject has a herpesvirus infection, and the method inhibits further herpesvirus infection in the subject.

9. The method of claim 8, wherein the subject has a latent herpesvirus infection.

10. The method of claim 1, wherein the inhibitor of Akt, or the inhibitor of a viral glycoprotein B, C, D or H, is applied systemically to the subject.

11. The method of claim 1, wherein the inhibitor of Akt is applied to topically the subject.

12. The method of claim 1, wherein the inhibitor of Akt is applied to a mucous membrane of the subject.

13. The method of claim 1, wherein the inhibitor of Ak is applied to a genitalial surface of the subject.

14. The method of claim 1, wherein the inhibitor of Akt is a small organic molecule of 2,000 daltons or less.

\* \* \* \* \*